US008712796B2

(12) United States Patent
Moore et al.

(10) Patent No.: US 8,712,796 B2
(45) Date of Patent: *Apr. 29, 2014

(54) SYSTEMS, COMPUTER PROGRAMS, AND METHODS FOR CONTROLLING COSTS OF A HEALTHCARE PRACTICE

(71) Applicants: Terrance Moore, Oviedo, FL (US); Charles Lewis, Lake Mary, FL (US)

(72) Inventors: Terrance Moore, Oviedo, FL (US); Charles Lewis, Lake Mary, FL (US)

(73) Assignee: Jasos Intellectual Property LLC, Lake Mary, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/955,026

(22) Filed: Jul. 31, 2013

(65) Prior Publication Data

US 2013/0346096 A1 Dec. 26, 2013

Related U.S. Application Data

(63) Continuation of application No. 13/540,746, filed on Jul. 3, 2012, which is a continuation of application No. 13/103,761, filed on May 9, 2011, which is a continuation of application No. 11/924,751, filed on Oct. 26, 2007, now Pat. No. 7,941,356, which is a continuation of application No. 09/812,703, filed on Mar. 19, 2001, now Pat. No. 7,401,027, which is an application for the reissue of Pat. No. Re. 43,550.

(51) Int. Cl.
*G06Q 50/00* (2012.01)
(52) U.S. Cl.
USPC ........................................ 705/2; 705/3; 705/4
(58) Field of Classification Search
CPC .............................. G06Q 50/22; G06F 19/322
USPC ......................................................... 705/2–4
See application file for complete search history.

(56) References Cited

U.S. PATENT DOCUMENTS

| 5,365,425 | A | 11/1994 | Torma et al. |
| 5,535,118 | A | 7/1996 | Chumbley |
| 5,557,514 | A | 9/1996 | Seare et al. |
| 5,706,441 | A | 1/1998 | Lockwood |
| 5,722,416 | A | 3/1998 | Swanson et al. |
| 5,722,418 | A | 3/1998 | Bro |
| 5,724,379 | A | 3/1998 | Perkins et al. |
| 5,737,539 | A | 4/1998 | Edelson et al. |

(Continued)

OTHER PUBLICATIONS

Declaration of Richard G. Fiscella, Jun. 11, 2007 (79 pages).

(Continued)

*Primary Examiner* — Luke Gilligan
(74) *Attorney, Agent, or Firm* — Bracewell & Giuliani LLP

(57) ABSTRACT

Systems, computer programs, and methods for controlling ancillary medical costs of a healthcare practice and/or insurance network with a plurality of physicians participating therein, are provided. According to an example method, the steps include identifying one or more a plurality of physicians having ancillary medical costs that exceed a certain level to thereby identify the physician or physicians for behavior modification with respect to ancillary medical costs. The method can also include generating information identifying recommended alternative ancillary medical procedures to modify behavior of a physician or physicians with respect to management of the ancillary medical costs. The method can also determining whether the ancillary medical costs of the physician or physicians have decreased to a preselected/baseline level, and distributing a percentage of a savings attributed to the modified ancillary medical cost management behavior when the ancillary medical costs have decreased to or below the preselected/baseline level.

13 Claims, 7 Drawing Sheets

(56) References Cited

U.S. PATENT DOCUMENTS

| | | | |
|---|---|---|---|
| 5,784,635 A | 7/1998 | McCallum | |
| 5,835,897 A | 11/1998 | Dang | |
| 5,918,208 A | 6/1999 | Javitt | |
| 5,924,073 A | 7/1999 | Tyuluman et al. | |
| 5,953,704 A | 9/1999 | McIlroy et al. | |
| 6,000,828 A | 12/1999 | Leet | |
| 6,012,035 A | 1/2000 | Freeman, Jr. et al. | |
| 6,014,631 A | 1/2000 | Teagarden et al. | |
| 6,026,364 A | 2/2000 | Whitworth | |
| 6,029,138 A | 2/2000 | Khorasani et al. | |
| 6,055,511 A | 4/2000 | Luebbering et al. | |
| 6,081,809 A | 6/2000 | Kumagai | |
| 6,112,182 A | 8/2000 | Akers et al. | |
| 6,112,183 A | 8/2000 | Swanson et al. | |
| 6,151,581 A | 11/2000 | Kraftson et al. | |
| 6,195,612 B1 | 2/2001 | Pack-Harris | |
| 6,223,164 B1 | 4/2001 | Seare et al. | |
| 6,302,844 B1 | 10/2001 | Walker et al. | |
| 6,370,511 B1 | 4/2002 | Dang | |
| 6,381,576 B1 | 4/2002 | Gilbert | |
| 6,385,589 B1 | 5/2002 | Trusheim et al. | |
| 7,311,666 B2 | 12/2007 | Stupp et al. | |
| 7,379,885 B1 | 5/2008 | Zakim | |
| 7,389,245 B1* | 6/2008 | Ashford et al. | 705/2 |
| 7,398,217 B2 | 7/2008 | Lewis et al. | |
| 7,401,027 B2 | 7/2008 | Moore et al. | |
| 7,426,474 B2 | 9/2008 | Schoenbaum et al. | |
| 2001/0037216 A1 | 11/2001 | Oscar et al. | |
| 2001/0041990 A1 | 11/2001 | Javitt | |
| 2002/0026478 A1 | 2/2002 | Rodgers et al. | |
| 2002/0111826 A1 | 8/2002 | Potter et al. | |
| 2002/0120468 A1 | 8/2002 | Atallah | |
| 2002/0133379 A1 | 9/2002 | Lewis et al. | |
| 2002/0138303 A1 | 9/2002 | Enos et al. | |
| 2002/0152097 A1 | 10/2002 | Javors | |
| 2002/0161779 A1* | 10/2002 | Brierley et al. | 707/103 R |
| 2007/0250343 A1 | 10/2007 | Sohal | |
| 2008/0059248 A1 | 3/2008 | Lewis et al. | |
| 2008/0097790 A1 | 4/2008 | Moore et al. | |
| 2008/0243546 A1 | 10/2008 | Ashford et al. | |
| 2010/0174561 A1 | 7/2010 | Moore et al. | |

OTHER PUBLICATIONS

Declaration of Richard G. Fiscella, Feb. 9, 2006 (27 pages).
Declaration of Richard G. Fiscella, Mar. 16, 2007 (19 pages).
Declaration of Richard G. Fiscella, Sep. 21, 2005 (5 pages).
Declaration of Richard G. Fiscella, Jun. 17, 2005 (31 pages).
Declaration of Richard G. Fiscella, Aug. 8, 2013 (13 pages).
Declaration of Armando Fuentes, Feb. 10, 2006 (27 pages).
Declaration of Armando Fuentes, Oct. 21, 2005 (5 pages).
Declaration of Armando Fuentes, Jul. 12, 2005 (31 pages).
Declaration of Armando Fuentes, Aug. 19, 2013 (13 pages).
Declaration of Charles C. Lewis and Terrance Moore, Nov. 19, 2004 (150 pages).
Information Disclosure Declaration of Charles C. Lewis and Terrance Moore, Dec. 26, 2001 (18 pages).
Declaration of Charles C. Lewis, Feb. 9, 2006 (27 pages).
Declaration of Charles C. Lewis, Sep. 20, 2005 (5 pages).
Declaration of Charles C. Lewis, Jul. 8, 2005 (31 pages).
Office Action in co-pending U.S. Appl. No. 11/933,075 dated Sep. 27, 2011.
Kelly Greene, Ga. Considers Network to Cut Medicaid Costs, Jan. 20, 1999, Wall Street Journal (Eastern Edition), p. S.1, Retrieved May 31, 2011 from ABI/INFORM Global (Document ID:38172220).
Rosenthal, Risk Sharing in Managed Care, Ph.D. dissertation, Harvard University,United States, Massachusetts, Retrieved May 31, 2011 from Dissertations & Theses: Full Text (Publication No. AAT9910116).
Office Action for co-pending U.S. Appl. No. 12/837,290 dated Dec. 8, 2011.
Higgins, M,. "Securing the perimeter", Health Management Technology; Atlanta; Dec. 2000; vol. 21; Issue 12, pp. 8-12.

Landon, "A Conceptual Mode of the Effects of Health Care Organizations on the Quality of Medical Care", May 1998, JAMA, vol. 270, No. 17, pp. 1377-1382.
Rice, "Physicians Payment Policies", 1997 Annual Review Public Health, pp. 549-565.
Glass, "Incentive-Based Physician Compensation Model", Jul. 1999, Journal of Ambulatory Care Management, pp. 36-40.
Segal, "Influencing Physicians Prescribing", Oct. 1999, Pharmacy Practice Management Quarterly, pp. 30-50.
Cherney, "Choosing an Advantageous Rick-Sharing Arrangement", Mar. 1999, Healthcare Financial Management, pp. 35-37.
Rosenstein, "Changing Physicians Behavior is Tool to Reduce Health Care Cost", Sep. 1991, Healthcare Strategic Management, vol. 9, Issue 9, pp. 14-16.
Snail, "The Effects of Hospital Contracting for Physicians Services on Hospital Performance", Spring 2000, University of California, Berkley, pp. 1-182.
Young, "Aligning Physician Financial Incentives in a Mixed-Payment Environment", Oct. 2000, Healthcare Financial Management, pp. 46-55.
Davis, "New Compensation Model Improves Physician Productivity", Jul. 1999, Healthcare Financial Management, pp. 46-49.
Shulkin, "Promoting Cost Effective Physician Behavior", Jul. 1993, Healthcare Financial Management, vol. 47, No. 7, pp. 48-54.
Schwartz, "Creating a Benchmark Database", Jan. 1998, Health Management Technology, pp. 65-66.
Office Action in co-pending U.S. Appl. No. 11/933,075 dated Dec. 21, 2010.
Office Action in co-pending U.S. Appl. No. 12/683,252 dated Dec. 15, 2010.
"Celadon Health Signs with Symmetry; Physician Incentive System Will Use Episode Treatment Groups (TM)", www.prnewswire.com, Phoenix, AZ.
Boyden, Andrew, et. al., "The Appropriate Use of Financial Incentives to Encourage Preventive Care in General Practice", Centre for Health Program Evaluation, May 2000, Research Report 18, Australia.
Smith, David, "Think Twice Beore Assuming Rick for Pharmacy Costs", Family Practice Management, 1999, http://www.aafp.org/fpm/990600fm/17.html.
Office Action in co-pending U.S. Appl. No. 11/933,075 dated Apr. 2, 2010.
Final Office Action for co-pending U.S. Appl. No. 13/103,761 dated Jan. 24, 2012.
Information Disclosure Declaration of Charles C. Lewis and Terrance Moore.
Office Action in co-pending U.S. Appl. No. 13/103,761 dated Jul. 20, 2011.
Office Action in co-pending U.S. Appl. No. 11/924,751 dated May 26, 2010.
Office Action in co-pending U.S. Appl. No. 09/812,703 dated Apr. 9, 2003.
Office Action in co-pending U.S. Appl. No. 09/812,703 dated Sep. 9, 2003.
Office Action in co-pending U.S. Appl. No. 09/812,703 dated Mar. 15, 2004.
Office Action in co-pending U.S. Appl. No. 09/812,703 dated Oct. 6, 2004.
Office Action in co-pending U.S. Appl. No. 09/812,703 dated Aug. 10, 2005.
Office Action in co-pending U.S. Appl. No. 09/812,703 dated May 31, 2006.
Office Action in co-pending U.S. Appl. No. 09/812,703 dated Sep. 12, 2006.
Office Action in co-pending U.S. Appl. No. 09/812,703 dated Apr. 9, 2007.
Office Action in co-pending U.S. Appl. No. 11/933,075 dated Jun. 1, 2012.
Office Action in co-pending U.S. Appl. No. 09/812,704 dated Apr. 1, 2003.
Office Action in co-pending U.S. Appl. No. 09/812,704 dated Dec. 5, 2003.

(56) References Cited

OTHER PUBLICATIONS

Office Action in co-pending U.S. Appl. No. 09/812,704 dated May 6, 2004.
Office Action in co-pending U.S. Appl. No. 09/812,704 dated Aug. 26, 2004.
Office Action in co-pending U.S. Appl. No. 09/812,704 dated Feb. 25, 2005.
Office Action in co-pending U.S. Appl. No. 09/812,704 dated Apr. 19, 2006.
Office Action in co-pending U.S. Appl. No. 09/812,704 dated Aug. 24, 2006.
Office Action in co-pending U.S. Appl. No. 09/812,704 dated Jan. 18, 2007.
File History of Moore U.S. Appl. No. 13/103,761.
File History of Moore U.S. Appl. No. 11/924,751.
File History of Moore U.S. Appl. No. 09/812,751.
File History of Moore U.S. Appl. No. 12/837,290.
File History of Lewis U.S. Appl. No. 11/933,075.
File History of Lewis U.S. Appl. No. 09/812,703.
File History of Lewis U.S. Appl. No. 12/832 813.

\* cited by examiner

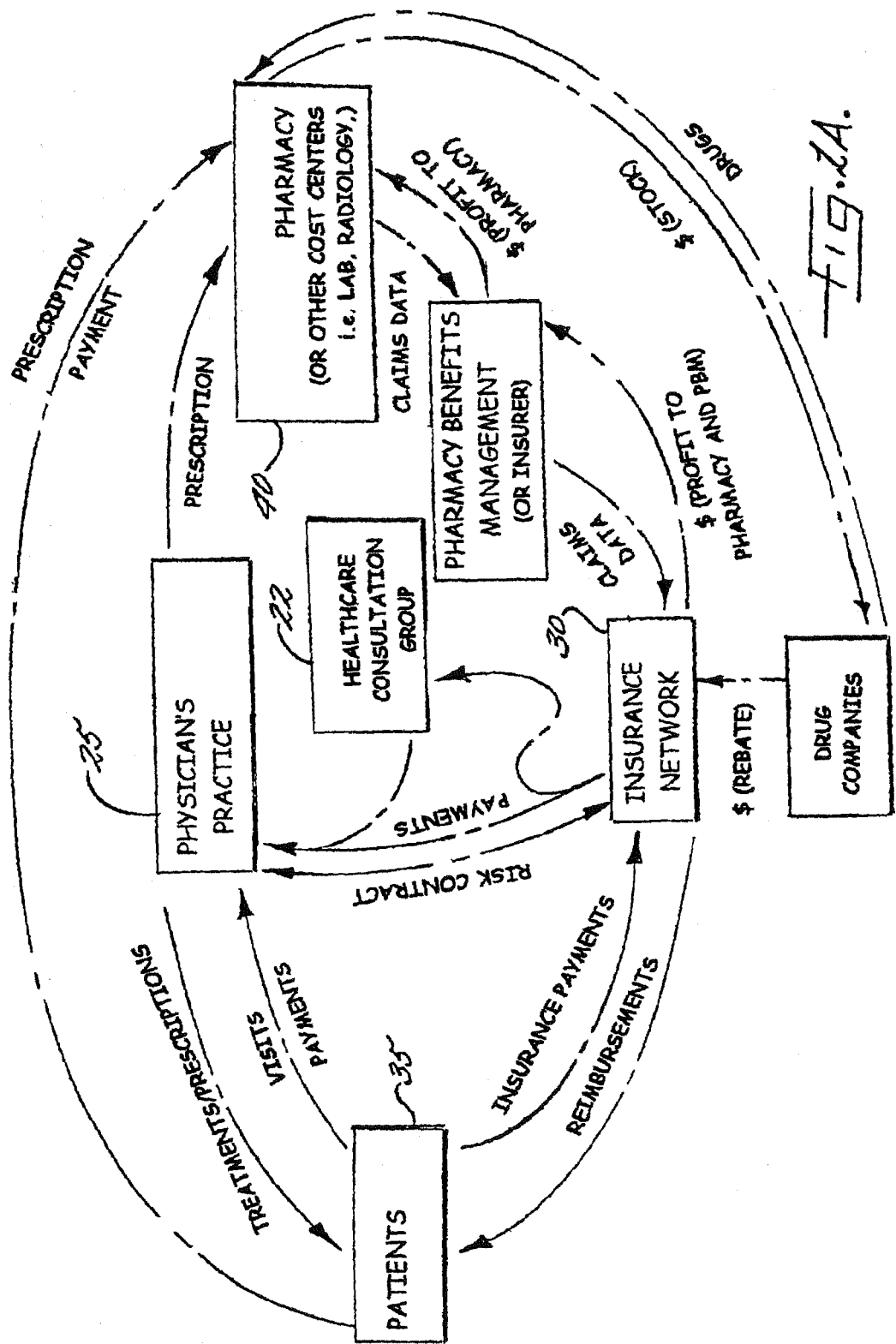

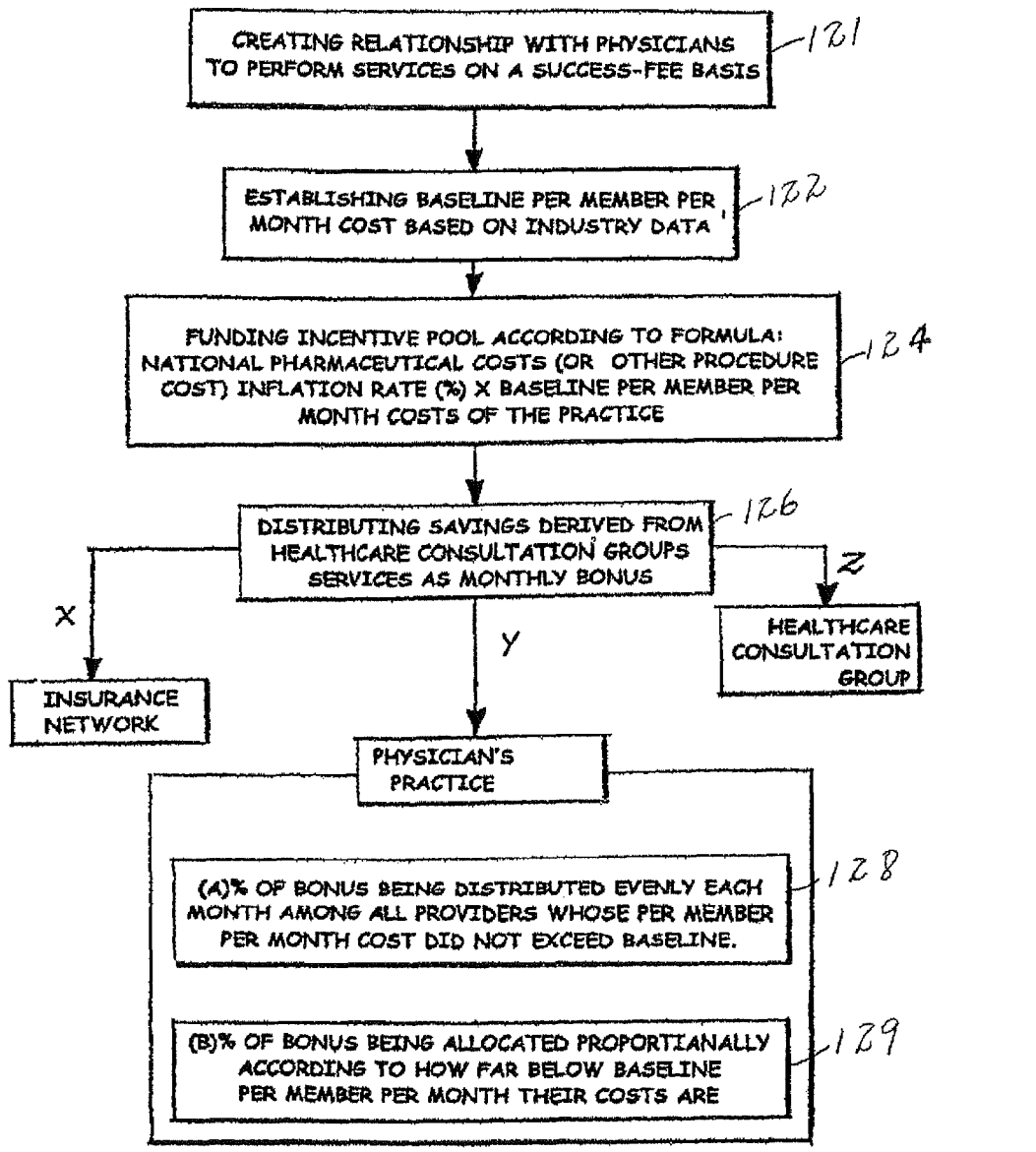

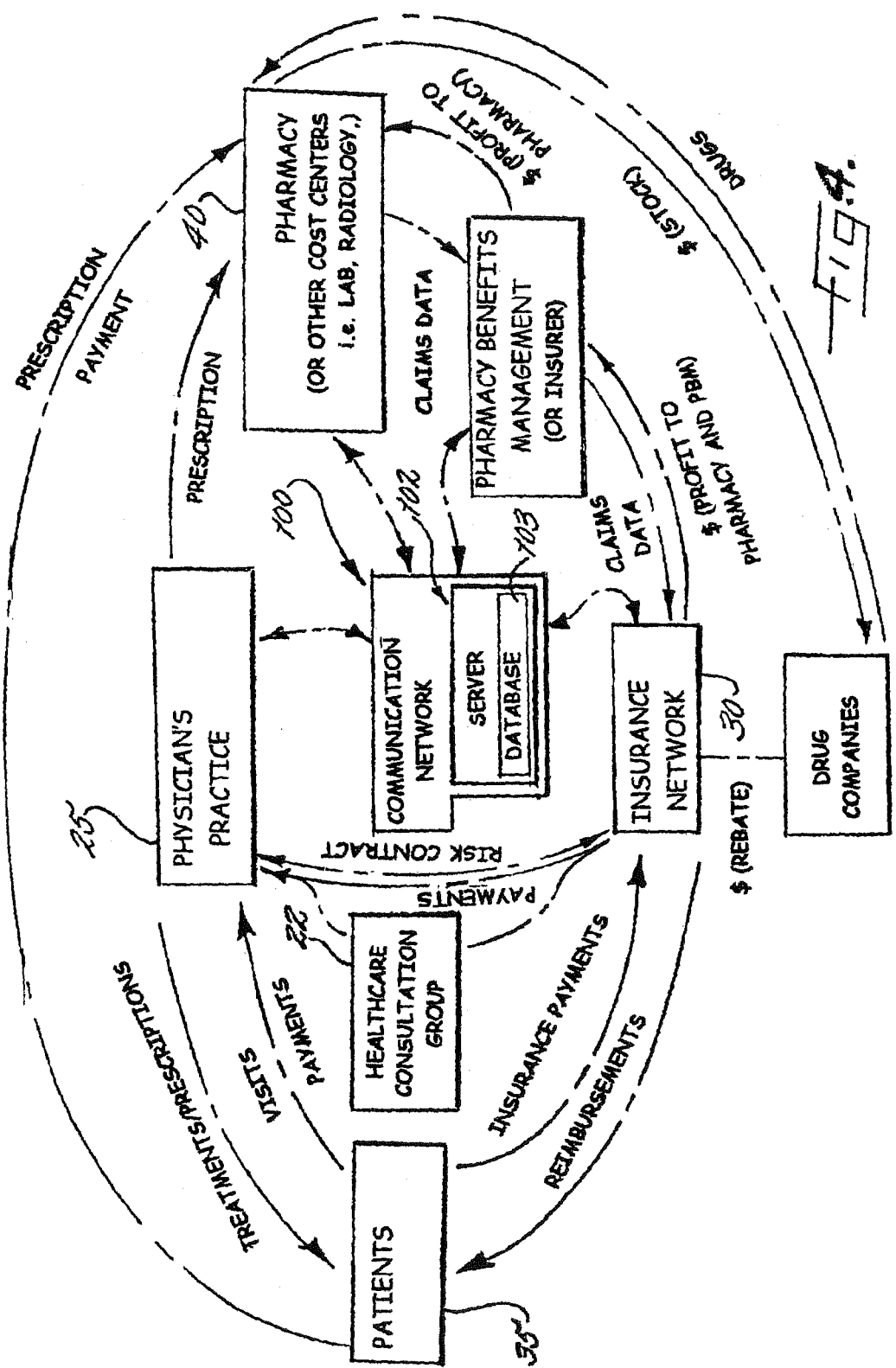

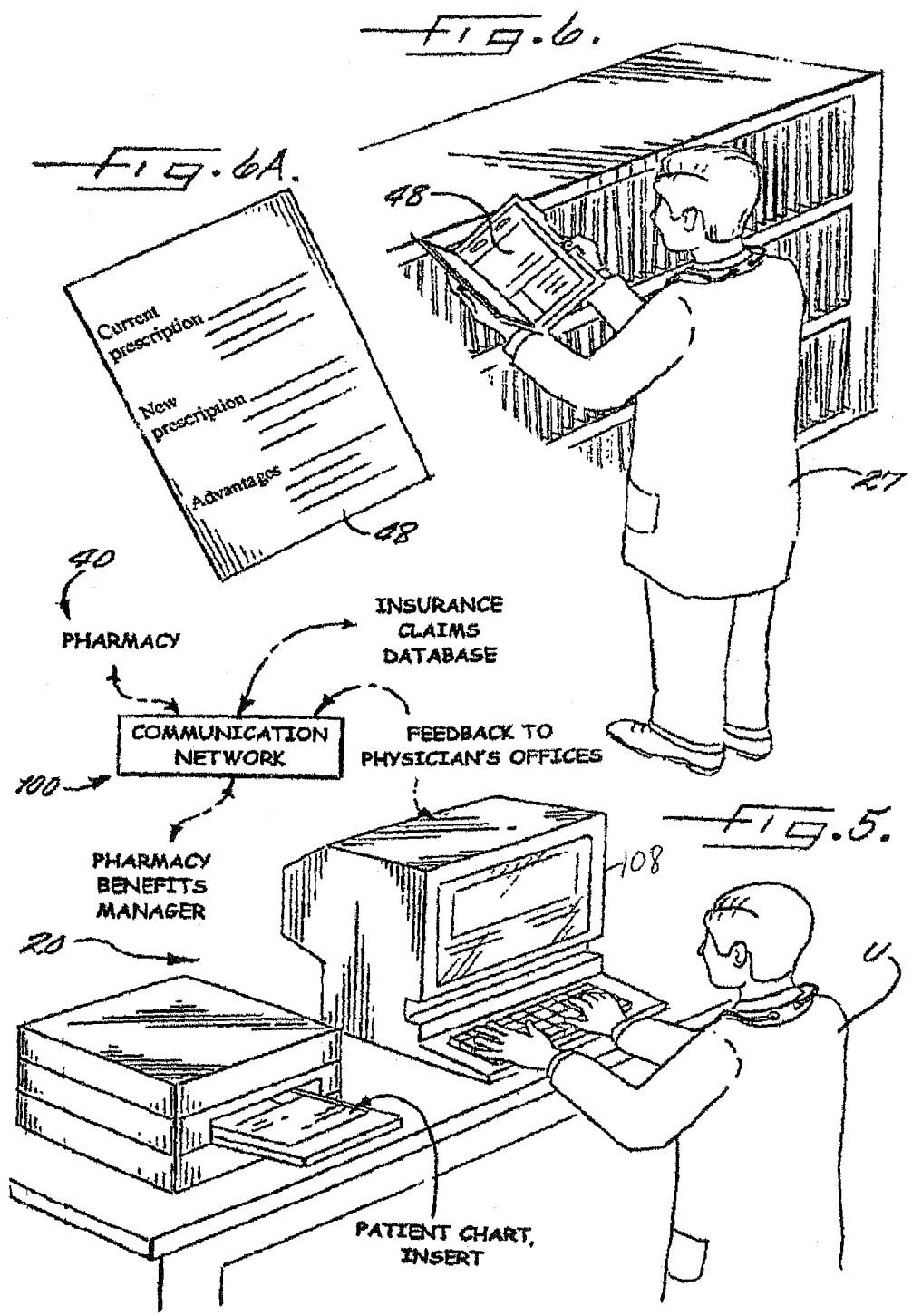

US 8,712,796 B2

SYSTEMS, COMPUTER PROGRAMS, AND METHODS FOR CONTROLLING COSTS OF A HEALTHCARE PRACTICE

RELATED APPLICATIONS

This application is a continuation of and claims the benefit of and priority to U.S. patent application Ser. No. 13/540,746, titled "Systems, Computer Programs, and Methods for Controlling Cost of a Healthcare Practice," filed on Jul. 3, 2012, which is a continuation of and claims the benefit of and priority to U.S. patent application Ser. No. 13/103,761, titled "Computer Implemented Method and Computer Program Product for Collecting Fees for an Insurance Network," filed on May 9, 2011, which is a continuation of U.S. patent application Ser. No. 11/924,751, titled "Methods for Collecting Fees for Healthcare Management Group" filed on Oct. 26, 2007, now U.S. Pat. No. 7,941,356, which is a continuation of U.S. patent application Ser. No. 09/812,703 titled "Methods for Collecting Fees for Healthcare Management Group" filed on Mar. 19, 2001, now U.S. Pat. No. 7,401,027, reissued as RE43,550; and is also related to U.S. patent application Ser. No. 09/812,704, titled "Methods and Systems for Healthcare Practice Management" also filed on Mar. 19, 2001, now U.S. Pat. No. 7,398,217, reissued as RE42,508, each of which is incorporated herein by reference in its entirety.

BACKGROUND OF THE INVENTION

1. Field of the Invention

The present invention relates to the healthcare industry and, more particularly, to the field of healthcare practice cost control and management.

2. Description of Related Art

In the healthcare industry, as illustrated in FIG. 1, physicians generally organize themselves into practice groups 25 and normally subcontract to an insurance network 30. The insurance network 30 is not limited to traditional insurance networks, i.e., Blue Cross Blue Shield, Aetna, United Healthcare, etc., but also includes self insured networks within companies, employers, or other large entities. The insurance network 30 includes a plurality of patients 35 that obtain healthcare services from the plurality of physicians 25 participating in the insurance network 30. The groups of physicians 25 include a plurality of physicians 25 that provide healthcare services to a plurality of patients 35 within a particular geographical area in varying medical fields. The physicians in the healthcare practices 25 are normally compensated a predetermined reimbursement amount by the insurance network 30 for every subscribing patient 35 in the insurance network 30 that is to be treated by the physicians 25.

For example, a physician 25 participating in the insurance network 30 may be reimbursed $80 per month by the insurance network 30 for agreeing to treat a patient 35 in the insurance network 30 and assume the responsibility for a percentage of the ancillary medical costs for that patient 25. As illustrated in FIG. 1, there exists a relationship between the insurance network 30 and the physician practice 25. Likewise, there also exists a relationship between the patients 35 and the insurance network 30, and the patients 35 and the physician practices 25. The physician practice 25 normally receives payment for services directly from the patients 35 or through reimbursements from the insurance network 30. The payment that is received from the patient 35 can be in the form of a co-payment or a partial payment for the healthcare services. In order for the physician practice 25 participating in the insurance network 30 to receive the entire reimbursement from the insurance network 30, i.e., the $80 per month for agreeing to treat each patient 35, the physician practice 25 must comply with preselected requirements set by the insurance network 30. These requirements often fall within varying cost centers, such as pharmaceutical, laboratory, anesthesiology, and radiation costs, for example.

In the pharmaceutical area, for example, a wide variety of prescription medications are developed and manufactured to combat similar illnesses. As illustrated in FIG. 1, prescription medication manufacturers 24 sometimes enter into agreements with the insurance network 30. The prescription medication manufacturers 24 sometimes offer rebates to insurance networks 30 if the physician practice 25 prescribes their medications. The prescription medication manufacturers 24 cannot enter into these types of agreements with the physician practices 25, as it would likely be contrary to public policy. The insurance network 30, in turn may enter into an agreement with a pharmacy network 21, such as a pharmacy benefits management (PBM), for example, to encourage the physician practice 25 in the insurance network 30 to prescribe certain medications. The PBM is compensated a profit on the preferred prescription medications, and a portion of the profits are then passed along to the pharmacy 40. The requirements, or preferences, set by the insurance network 30 regarding pharmaceutical costs, for example, include the types of prescription medications that the physicians may prescribe to their patients.

In some instances, the insurance networks provide incentives to the physician practice 25 for prescribing medications upon which, the insurance network 30 receives discounts from prescription medication manufacturers 24. If the physician practice 25 bears any percentage of medication costs for the patient 35 and prescribes medications which differ from those preferred by the insurance network 30, the incentives may be withheld from the physician practice 25, i.e., the physician practice 25 may be paid nothing instead of $10 for the patient 35 in the insurance network 30. As illustrated in FIG. 1, the insurance network 30 monitors the prescriptions that the physician practice 25 participating in the insurance network 30 writes through a monitoring relationship developed with pharmacies 40 and pharmacy networks 21. In this monitoring relationship, the pharmacy 40 and the PBM provide claims data to the insurance network 30.

There are many different levels of risk for the physician practice 25 that is associated with this arrangement. If the insurance network 30 assumes the financial responsibility for the patient's 35 healthcare needs, then the physician practice 25 assumes no risk. If, however, the physician practice 25 assumes the financial responsibility for the patient's healthcare needs, i.e., any healthcare costs beyond the reimbursement amount from the insurance network 30, then the physician practice 25 assumes the most risk. Another alternative arrangement is if the financial responsibility for the patient's 35 healthcare needs is shared between the physician practice 25 and the insurance network 30. In such an arrangement, the risk for patient's 35 healthcare costs is shared between the insurance network 30 and the physician practice 25. As illustrated in FIG. 1, the payments between the insurance network 30 and the physician practice 25 can vary depending upon the amount of risk taken by the physician practice 25.

As further illustrated in FIG. 1, patients 35 participating in the insurance network 30 obtain healthcare treatment from the physician practice 25 and pay premiums or insurance payments to the insurance network 30. The medical treatment provided to the patients 35 by the physicians in the physician practice 25 can include prescribing medications. The patients 35, however, obtain the prescription medications from the pharmacy 40 and provide either a full payment or a co-payment for the prescription medications. The patient 35 can then be reimbursed for some or all of the payment for the prescription medications from the insurance network 30.

This arrangement is disadvantageous for the physician practice 25 participating in the insurance network 30 because it requires a great deal of management and organization to follow the requirements of the insurance network 30. The system is even more disadvantageous for the physician practice 25 if it participates in multiple insurance networks 30. Each insurance network 30 maintains a preferred list of prescription medications, for example, that the physician practice 25 may prescribe to the patients 35. Further, each insurance network 30 updates their preferred list of prescription medications on a routine basis. The physician practice 25 in the insurance network 30 generally attempts to spend the majority of their time treating patients 35. The management and organization of the insurance network 30 requirements can be time consuming and eliminate some of the time that a physician practice 25 may normally dedicate to the treatment of patients 35.

Traditionally, there also has been tension between the physician practice 25 and the insurance network 30. The tension can be caused by the insurance network 30 delaying payment to the physician practice 25 with notification of a particular network requirement that has been violated, if any. In addition, the physician practice 25 normally receives very little support from the insurance network 30, such as patient history updates and information on medication costs. Tensions are also sometimes caused by the insurance network's 30 perception that the physician practice 25 over-bills for treatment and does not provide all possible treatment options for patients 35. The physician practice 25 sometimes feels pressured by the insurance network 30 to provide medical treatment to their patients 35 according to the preferences of the insurance network 30 instead of according to their own medical judgments. Of course, the physician practice 25 is free to independently treat the patients 35 in the insurance network 30 based on medical judgment, but the tension between the physician practice 25 and the insurance network 30 still exists.

The physician practice 25 is not bound by the treatment procedures that are preferred by the insurance network 30. Often, however, conflict between the insurance network 30 and the physician practice 25 can arise when the insurance network 30 prefers the physician practice 25 to perform certain medical procedures or prescribe particular medications that are more profitable to the insurance network 30. The physician practice 25 does not have the time necessary to perform the exhaustive research necessary to determine if the treatment proposed by the insurance network 30 is feasible, or even safe, to patients 35. Prudent physicians in the physician practice 25 often do not change their treatment practices based simply on information provided by the insurance networks 30.

In the interest of patient safety, physicians in the physician practice 25 should research medical literature to become more educated as to possible benefits of alternative medications. As noted above, however, this takes a great deal of time that can better be used to treat patients 35. In order to conserve the time that might normally be spent on managing and organizing the insurance network 30 requirements, however, some physician practices 35 may hire office managers. This is disadvantageous because an office manager can be extremely costly and will normally need office space. The office space that may be used by the proposed office manager may be an examination room in which the physician would normally treat patients 35. Once again, this cuts down on the number of patients 35 that the physician practice 25 can possibly treat. The office manager also often only manages finances and personnel and has little understanding of physician practices 25 with respect to relationships between insurance networks 30 and physicians' 25 decisions and practices with respect to patients 30.

It has been proposed that the performance of a first healthcare provider can be compared to the performance of a second healthcare provider using a computer program as described in U.S. Pat. No. 5,652,842 titled "Analysis and Reporting of Performance of Service Providers", by Siegrist, Jr. et al. More particularly, a method of monitoring customer satisfaction so as to keep the healthcare providers competitive in many different fields is described. The method described in Siegrist, Jr. et al., however, is disadvantageous to group physicians in organizing and managing healthcare costs that are dependant upon preferred treatment of the insurance network.

Often times, in an effort to become more profitable, a healthcare practice 25 or a self insured employer may study the current relationship between the healthcare practice group 25 and the insurance network 30 or hire a business consultant to analyze this relationship and make recommendations as to how to become more profitable. This, however, is disadvantageous because the business consultant does not have accountability for the results. In other words, the business consultant analyzes the situation, makes a recommendation, and collects a fee for the time spent in analyzing the situation. This is normally the end of the relationship between the business consultant and the physician 25. The responsibility for implementation is then shifted to the healthcare practice 25, with some added knowledge provided by the business consultant who has collected a fee and exited the situation, to make the practice more profitable with no assistance.

Hiring a business consultant is also disadvantageous because the healthcare practice 25 has to assume risk for engaging the business consultant to review the healthcare practice 25. This is also disadvantageous because prudent physicians will normally take time to evaluate the expertise of the business consultant if the situation calls for the healthcare practice 25 to assume a risk. This is further disadvantageous because the healthcare practice 25 is left with the responsibility of implementing the suggestions of the business consultant in cases where the consultant merely analyzes the situation and provides information.

When the physician practice 25 is not able to organize and manage medical treatment information in a manner that is preferred by the insurance network 30 in which they participate, there only exist two possible results. Either the physician practice 25 receives lower reimbursements from the insurance network 30, or the insurance network 30 is less profitable. No matter which result occurs, however, the ultimate end result is higher medical costs for patients 35. Therefore, the patients 35 are the real losers in the situations described above.

SUMMARY OF THE INVENTION

With the foregoing in mind, embodiments of the present invention advantageously provide a system and methods for optimizing profits of a healthcare practice. The system and methods can also advantageously assist physicians and insurance providers in providing cost-effective healthcare services to patients. Various embodiments of the present invention additionally advantageously eliminate the time necessary for physicians to conduct exhaustive research in determining if alternative, and more profitable, ancillary medical procedures are beneficial to their patients. Various embodiments of the present invention also advantageously substantially reduces manpower, expense, and tool-development necessary to implement management changes that decrease healthcare costs. The system and methods according to embodiments of the present invention further advantageously can assist in controlling the rising costs of medical care by reducing physicians' ancillary medical costs. Various embodiments of the present invention still further advantageously can strengthen the relationship between physicians and insurance providers by providing an intermediary between the two.

Various embodiments of the present invention also advantageously can decrease financial risk for a healthcare practices or an insurance network in engaging a healthcare consultation group to manage healthcare costs. Various embodiments of the present invention also advantageously can provide a pricing, billing, or charging structure that can provide accountability to a healthcare consultation group. If the healthcare consultation group can be held accountable for performance, then healthcare practices and insurance networks are more likely to trust the healthcare consultation group. Further, the healthcare practice and the insurance network are provided an incentive to employ the services of the healthcare consultation group.

More particularly, various embodiments of the present invention provide a method of healthcare practice management which can include collecting fees for managing and optimizing the profitability of a plurality of physicians in a healthcare practice participating in an insurance network. According to an embodiment of the present invention, the method includes receiving, by a computer, data indicating ancillary medical costs attributed to a plurality of physicians in a healthcare practice participating in an insurance network, and identifying by the computer one or more the plurality of physicians in the healthcare practice participating in the insurance network having ancillary medical costs that exceed a certain level to thereby identify one or more of the plurality of physicians in the healthcare practice for behavior modification with respect to ancillary medical costs to thereby reduce ancillary medical costs attributable to the respective one or more physicians. The method also includes generating information identifying recommended alternative ancillary medical procedures to modify behavior of the one or more of the plurality of physicians in the healthcare practice with respect to management of the ancillary medical costs, determining, by the computer, whether the ancillary medical costs of the one or more of the plurality of physicians in the healthcare practice have decreased to a preselected level, and distributing a percentage of a savings attributed to the modified ancillary medical cost management behavior of the one or more of the plurality of physicians when the ancillary medical costs of the respective one or more of the plurality of physicians in the healthcare practice have decreased to or below the preselected level.

According to another embodiment of the present invention, the method includes the step of establishing a relationship between a healthcare consultation group and the healthcare practice participating in the insurance network to increase the physician's profitability by reducing a risk of not receiving a predetermined reimbursement amount for ancillary medical costs from the insurance network. The method can also includes the step of distributing predetermined percentages of savings attributed to the physicians' modified ancillary medical cost management behavior. The method can also advantageously include the step of funding an incentive pool to be paid to the healthcare practice participating in the insurance network if the healthcare costs of the plurality of physicians in the healthcare practice decrease to a predetermined level over a preselected period of time.

According to another embodiment of the present invention, the method includes the steps of establishing a relationship between a healthcare consultation group and the healthcare practice participating in the insurance network and funding an incentive pool to pay funds to the healthcare practice participating in the insurance network if the ancillary medical costs of the plurality of physicians in the healthcare practice have not decreased to the predetermined level over the preselected period of time. The method also includes the steps of gathering data from each of the plurality of physicians in the healthcare practice including management of ancillary medical costs respective to the physicians, modifying ancillary medical cost management behavior of at least one of the plurality of physicians in the healthcare practice by the healthcare consultation group responsive to the data gathered to thereby reduce ancillary medical costs of the plurality of physicians in the healthcare practice to a predetermined level. The method further includes determining whether the ancillary medical costs of the plurality of physicians in the healthcare practice have reached a predetermined level within a preselected period of time, paying funds from the funded incentive pool to the healthcare practice if the ancillary medical costs of the plurality of physicians in the healthcare practice have not decreased to the predetermined level over the preselected period of time, and distributing a predetermined percentage of savings attributed to the modifying ancillary medical cost management behavior of at least one of the plurality of physicians if the ancillary medical costs of the plurality of physicians in the healthcare practice have decreased to the predetermined level over the preselected period of time.

Various embodiments of the present invention provide a method of healthcare practice management which can include collecting fees for managing a plurality of physicians in a healthcare practice participating in an insurance network. According to an embodiment of the present invention, the method includes the steps of establishing a relationship between a healthcare consultation group and the healthcare practice participating in the insurance network and funding an incentive pool to pay funds to the healthcare practice when or if ancillary medical costs of the plurality of physicians in the healthcare practice do not decrease to a predetermined level over a preselected period of time. The method also includes the steps of gathering data in a tangible computer medium from each of the plurality of physicians in the healthcare practice, including ancillary medical costs respective to the physicians, and establishing a plan to pay funds from the funded incentive pool to the healthcare practice when or if ancillary medical costs of the plurality of physicians in the healthcare practice do not decrease to a predetermined level over a preselected period of time. The method also includes modifying ancillary medical cost management behavior of at least one of the plurality of physicians in the healthcare practice by the healthcare consultation group responsive to the data gathered in the tangible computer medium to thereby reduce ancillary medical costs of the plurality of physicians in the healthcare practice to a predetermined level, determining whether the ancillary medical costs of the plurality of physicians in the healthcare practice have reached the predetermined level within the preselected period of time, and distributing predetermined percentages of savings attributed to the modifying ancillary medical cost management behavior of the plurality of physicians to one or more of the healthcare consultation group, the healthcare practice, and the insurance network, or combination thereof, if the ancillary medical costs have decreased to the predetermined level over the preselected period of time.

Various embodiments of the present invention also advantageously provide a method of collecting fees for managing and optimizing the profitability of an insurance network having a plurality of physicians in a healthcare practice participating therein. According to an embodiment of the present invention, the method includes gathering, by a computer, data indicating ancillary medical costs attributed to a plurality of physicians in a healthcare practice participating in an insurance network, and identifying by the computer one or more the plurality of physicians in the healthcare practice participating in the insurance network having ancillary medical costs that exceed a certain level to thereby identify one or more of the plurality of physicians in the healthcare practice for behavior modification with respect to ancillary medical costs to thereby reduce ancillary medical costs attributable to the respective one or more physicians and to increase profitability of the one or more of the plurality of physicians. The method can also include generating information identifying recommended alternative ancillary medical procedures to modify behavior of the one or more of the plurality of physicians in the healthcare practice with respect to management of the ancillary medical costs, determining, by the computer, whether the ancillary medical costs of the plurality of physicians in the healthcare practice have been reduced to or below a ancillary medical costs baseline, and distributing a predetermined percentage of the savings attributed to the modified ancillary medical cost management behavior of the one or more of plurality of physicians if the ancillary medical costs have been reduced to or below the ancillary medical costs baseline.

According to another embodiment of the present invention, the method advantageously includes the step of establishing a relationship between a healthcare management consultation group and the healthcare practice participating in the insurance network to increase the insurance network's profitability by limiting the plurality of physicians' ancillary medical cost management behavior that is not preferred by the insurance network. The method also includes the step of distributing predetermined percentages of savings attributed to the physicians' modified ancillary medical cost management behavior.

According to another embodiment of the present invention, the method includes the steps of establishing a relationship between a healthcare management consultation group and the healthcare practice participating in the insurance network, gathering data in a tangible computer medium from each of the plurality of physicians in the healthcare practice participating in the insurance network regarding management of ancillary medical costs respective to the physicians, and modifying ancillary medical cost management behavior of at least one of the plurality of physicians in the healthcare practice by the healthcare consultation group responsive to the data gathered in the tangible computer medium to thereby reduce ancillary medical costs of the plurality of physicians in the healthcare practice to a predetermined level. The method also includes determining whether the ancillary medical costs of the plurality of physicians in the healthcare practice have reached the predetermined level within a preselected period of time and distributing from an incentive pool predetermined percentages of savings attributed to the modifying ancillary medical cost management behavior of the at least one of the plurality of physicians to at least one of the insurance network and the healthcare management consultation group when the ancillary medical costs have decreased to the predetermined level over the preselected period of time.

Various embodiments of the present invention provide computer-assisted methods of controlling costs of a plurality of physicians in a healthcare practice participating in an insurance network. An exemplary embodiment can include the steps of providing a first computer associated with a tangible non-transitory computer readable medium and positioned to receive data indicating management of ancillary medical costs by a plurality of physicians in a healthcare practice participating in an insurance network, receiving data by the first computer from at least one other computer associated with the plurality of physicians in the healthcare practice participating in the insurance network, whereby the received data includes ancillary medical costs attributed to the plurality of physicians, and identifying by the first computer one or more the plurality of physicians in the healthcare practice participating in the insurance network having ancillary medical costs that exceed a certain level to thereby identify one or more of the plurality of physicians in the healthcare practice for behavior modification with respect to ancillary medical costs to increase profitability of the one or more of the plurality of physicians thereby reducing a risk of the healthcare practice not receiving a predetermined reimbursement amount for ancillary medical costs from the insurance network. The method can also include generating information by the first computer identifying recommended alternative ancillary medical procedures to modify behavior of the one or more of the plurality of physicians in the healthcare practice with respect to management of the ancillary medical costs, determining by the first computer whether the ancillary medical costs of the one or more of the plurality of physicians in the healthcare practice have decreased to or below baseline ancillary medical costs, and calculating a percentage of a savings attributed to modified ancillary medical cost management behavior of the one or more of the plurality of physicians in the healthcare practice identified for behavior modification, for distribution to one or more of the following: the healthcare practice participating in the insurance network and the insurance network, when the ancillary medical costs of the respective one or more of the plurality of physicians in the healthcare practice have decreased to or below that of the baseline ancillary medical costs.

Another embodiment of the method can include providing a first computer associated with a tangible non-transitory computer readable medium and positioned to receive data indicating management of ancillary medical costs of a plurality of physicians in a healthcare practice participating in an insurance network, receiving data by the first computer for the plurality of physicians in the healthcare practice participating in the insurance network, whereby the received data includes ancillary medical costs attributed to the respective physicians, and identifying by the first computer one or more of the plurality of physicians in the healthcare practice participating in the insurance network having ancillary medical costs that exceed a certain level to thereby identify one or more of the plurality of physicians in the healthcare practice for behavior modification with respect to management of ancillary medical costs. The method can also include generating information identifying recommended alternative ancillary medical procedures by the first computer to modify behavior of the one or more of the plurality of physicians in the healthcare practice identified for behavior modification with respect to management of the ancillary medical costs to thereby reduce a risk of the healthcare practice not receiving a predetermined reimbursement amount for ancillary medical costs from the insurance network, determining by the first computer whether the ancillary medical costs of the one or more of the plurality of physicians in the healthcare practice identified for behavior modification have decreased to a level that is at or below a preselected level, and calculating a percentage of a savings attributed to modified ancillary medical cost management behavior of the one or more of the plurality of physicians in the healthcare practice identified for behavior modification, for distribution when the ancillary medical costs have decreased to a level that is at or below the preselected level.

Various embodiments of the present invention can advantageously include the formation of a team relationship working towards a common goal having aligned incentives, i.e., a team working towards the goal of enhancing profitability. Various embodiments of the present invention also advantageously provide accountability to the healthcare consultation group. Accountability will ease the minds of the healthcare practice and insurance network giving the healthcare consultation group a chance to prove that profits can be enhanced. This arrangement advantageously can allow all involved to gain, including patients through more cost-effective medical care. Various embodiments of the present invention can also advantageously eliminate the time necessary for healthcare practices and insurance networks to research references of the healthcare consultation group because there is no risk for the insurance network or the healthcare practice to engage the healthcare consultation group.

Furthermore, various exemplary embodiments of the present invention can beneficially include a computer implemented method for managing and optimizing the profitability of a plurality of physicians in a healthcare practice participating in an insurance network. Advantageously, such a computer implemented method can include, for example, the step of receiving, via a communications network, data for each of a plurality of physicians in a healthcare practice participating in an insurance network. Such data can include, by way of example, current ancillary medical procedures used by each of the plurality of physicians to treat one or more of a plurality of patients that obtain healthcare services from the plurality of physicians and ancillary medical costs respective to each of the plurality of physicians. Such an exemplary computer implemented method can also include the steps of comparing the data received via the communications network for each of the plurality of physicians in the healthcare practice with one or more preferred ancillary medical procedures of the insurance network, and identifying at least one of the plurality of physicians in the healthcare practice who engages in ancillary medical procedures that are not preferred by the insurance network. In addition, an exemplary computer implemented method to manage and optimize the profitability of a plurality of physicians in a healthcare practice can include, for example, the steps of recommending to the at least one of the plurality of physicians in the healthcare practice, via the communications network, alternative ancillary medical procedures that are preferred by the insurance network, and determining whether the ancillary medical costs of the at least one of the plurality of physicians in the healthcare practice participating in the insurance network has reached the predetermined level within a preselected period of time.

Advantageously, various exemplary embodiments of the present invention can also include, for example, a computer implemented method of managing a plurality of physicians in a healthcare practice participating in an insurance network. Such an exemplary embodiment of the present invention can include, by way of example, the steps of receiving, via a communications network, data for each of a plurality of physicians in a healthcare practice participating in an insurance network, and establishing a plan to pay funds from an incentive pool selectively funded by the healthcare consultation group to the healthcare practice when ancillary medical costs of the plurality of physicians in the healthcare practice do not decrease to a predetermined level over a preselected period of time. Beneficially, the data received via the communications network can include, for example, current ancillary medical procedures used by each of the plurality of physicians to treat one or more of a plurality of patients that obtain healthcare services from the plurality of physicians and ancillary medical costs respective to each of the plurality of physicians. Such a computer implemented method can also include, for example, the steps of comparing the data received via, the communications network for each of the plurality of physicians in the healthcare practice with one or more preferred ancillary medical procedures of the insurance network, and identifying at least one of the plurality of physicians in the healthcare practice who engages in ancillary medical procedures that are not preferred by the insurance network. Moreover, an exemplary computer implemented method according to the present invention can also include the steps of recommending to the at least one of the plurality of physicians in the healthcare practice, via the communications network, alternative ancillary medical procedures that are preferred by the insurance network to thereby reduce the ancillary medical costs of the at least one of the plurality of physicians in the healthcare practice to a predetermined level, and determining whether the ancillary medical costs of the at least one of the plurality of physicians in the healthcare practice participating in the insurance network has reached the predetermined level within a preselected period of time.

Various exemplary embodiments of the present invention can also include a computer implemented method of modifying the ancillary medical cost management behavior of at least one of physicians in a healthcare practice participating in an insurance network to thereby enhance the profitability of an insurance network. By way of example, such a computer implemented method can include the step of receiving, via a communications network, data for each of a plurality of physicians in a healthcare practice participating in an insurance network, the data including at least one of: current ancillary medical procedures used by each of the plurality of physicians to treat one or more of a plurality of patients that obtain healthcare services from the plurality of physicians, ancillary medical costs respective to each of the plurality of physicians, and the number of patients of each of the plurality of physicians participating in the insurance network. Furthermore, such a computer implemented method can also include, for example, the steps of comparing, in a first computer process, the data received via the communications network for each of the plurality of physicians in the healthcare practice with one or more preferred ancillary medical procedures of the insurance network, and identifying, in a second computer process, responsive to the first computer process, at least one of the plurality of physicians in the healthcare practice who engages in ancillary medical procedures that are not preferred by the insurance network.

In addition, a computer implemented method according to various exemplary embodiments of the present invention can also include, for example, the step of recommending, in a third computer process, to the at least one of the plurality of physicians in the healthcare practice, responsive to the second computer process via the communications network, alternative ancillary medical procedures that are preferred by the insurance network to thereby reduce the ancillary medical costs of the at least one of the plurality of physicians in the healthcare practice to a predetermined level and enhance the profitability of the insurance network. Advantageously, such an exemplary computer implemented method can also include the step of determining, in a fourth computer process, whether risk of the at least one of the plurality of physicians of not receiving a predetermined reimbursement amount for ancillary medical costs from the insurance has been reduced responsive to recommending, in the third computer process, alternative ancillary medical procedures to the at least one of the plurality of physicians in the healthcare practice.

Various embodiments of the present invention also include healthcare management systems for controlling costs of a plurality of physicians in a healthcare practice participating in an insurance network. An example of a system can include a computer to facilitate modifying ancillary medical cost management behavior of one or more of a plurality of physicians in a healthcare practice and to facilitate paying a percentage of savings attributed to modified ancillary medical cost management behavior of the one or more of plurality of physicians, the computer having a tangible storage medium for storing computer executable program code, and computer executable program code stored on the storage medium of the computer and comprising a set of instructions that, when executed by the computer, cause the computer to perform various operations. According to an embodiment, the operations can include receiving data from at least one other computer associated with the plurality of physicians in the healthcare practice participating in the insurance network, whereby the received data includes data indicating ancillary medical costs attributed to at least one of the plurality of physicians, and identifying one or more of the plurality of physicians in the healthcare practice participating in the insurance network that have ancillary medical costs that exceed a certain level to thereby identify one or more of the plurality of physicians in the healthcare practice for behavior modification with respect to ancillary medical costs. The operations can also include generating information identifying recommended alternative ancillary medical procedures with respect to management of the ancillary medical costs, determining whether the ancillary medical costs of the at least one of the plurality of physicians in the healthcare practice have decreased to a level that is at or below a preselected level, and calculating a percentage of a savings attributed to the modified ancillary medical cost management of the one or more of the plurality of physicians, for distribution to the healthcare practice when the ancillary medical costs of the one or more of the plurality of physicians in the healthcare practice have decreased to a level that is at or below the preselected level. The operations can also include distributing the preselected percentage of the savings attributed to the modified ancillary medical cost management of the one or more of the plurality of physicians when the ancillary medical costs of the one or more of the plurality of physicians in the healthcare practice have decreased to a level that is at or below the baseline ancillary medical cost.

According to another embodiment, the system can include a computer to facilitate modifying ancillary medical cost management behavior of one or more of a plurality of physicians in a healthcare practice and to facilitate paying a percentage of a savings attributed to modified ancillary medical cost management behavior of the one or more of the plurality of physicians in the healthcare practice; and computer executable program code stored on storage medium of the computer and comprising a set of instructions that, when executed by the computer, cause the computer to perform various operations. The operations can include receiving data for the plurality of physicians in the healthcare practice participating in the insurance network, identifying by the first computer one or more of the plurality of physicians in the healthcare practice participating in the insurance network having ancillary medical costs that exceed a certain level to thereby identify one or more of the plurality of physicians in the healthcare practice for behavior modification with respect to management of ancillary medical costs, generating information identifying recommended alternative ancillary medical procedures with respect to management of the ancillary medical costs, determining whether the ancillary medical costs of the one or more of the plurality of physicians in the healthcare practice have decreased to a level that is at or below the preselected level, and calculating a percentage of a savings attributed to modified ancillary medical cost management of the one or more of the plurality of physicians, for distribution when the ancillary medical costs have decreased to the preselected level. The operations can also include distributing the percentage of the savings attributed to the modified ancillary medical cost management behavior of the one or more of the plurality of physicians when the ancillary medical costs have decreased to a level that is at or below a baseline ancillary medical cost.

Various embodiments of the present invention provide a healthcare management system for enhancing profitability of an insurance network having a plurality of physicians in a healthcare practice participating in the insurance network. The system can include a computer configured to facilitate paying a percentage of a savings attributed to modified ancillary medical cost management behavior of one or more of the plurality of physicians, and computer executable program code stored on a storage medium of the computer and comprising a set of instructions that, when executed by the computer, cause the computer to perform various operations. The operations can include receiving data from at least one other computer associated with the plurality of physicians, whereby the received data indicates the ancillary medical costs attributed to at least one of the plurality of physicians in the healthcare practice participating in the insurance network. The operations can also include identifying by the first computer one or more of the plurality of physicians in the healthcare practice participating in the insurance network having ancillary medical costs that exceed a certain level to thereby identify one or more of the plurality of physicians in the healthcare practice for behavior modification with respect to management of ancillary medical costs, and generating information identifying alternative recommended ancillary medical practices to modify behavior of the one or more of the plurality of physicians in the healthcare practice with respect to management of the ancillary medical costs that is not preferred by the insurance network. The operations can further include determining whether the ancillary medical costs of the one or more of the plurality of physicians in the healthcare practice have decreased to a level that is at or below a preselected level, and calculating a percentage of the savings attributed to modified ancillary medical costs management of the one or more of the plurality of physicians for distribution to one or more of the following: the insurance network and a healthcare management consultation group when the ancillary medical costs have decreased to a level that is at or below the preselected level. The operations can still further include distributing the percentage of the savings attributed to the modified ancillary medical cost management behavior of the one or more of the plurality of physicians when the ancillary medical costs have decreased to a level that is at or below the preselected level.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 1A is a schematic view of a relationship between physicians, insurance networks, patients, and a healthcare consultation group according to an embodiment of the present invention;

FIG. 3 is a flow chart describing the method of managing ancillary medical costs and optimizing profitability for an insurance network according to an embodiment of the present invention;

FIG. 4 is a schematic view of a system for a healthcare practice including a plurality of physicians participating in an insurance network according to an embodiment of the present invention;

FIG. 5 is an environmental view of a physician accessing a communications network through a user interface of a system for a healthcare practice to obtain information regarding management of ancillary medical costs according to an embodiment of the present invention;

FIG. 6 is an environmental view of a physician researching an information card positioned in a patient's chart to determine if an alternative ancillary medical procedure is appropriate according to an embodiment of the present invention; and FIG. 6A is a front elevational view of an information card that can be positioned in a patient's chart according to an embodiment of the present invention.

DETAILED DESCRIPTION

The present invention will now be described more fully hereinafter with reference to the accompanying drawings which illustrate preferred embodiments of the invention. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, the prime notation, if used, indicates similar elements in alternative embodiments.

Figure 1:
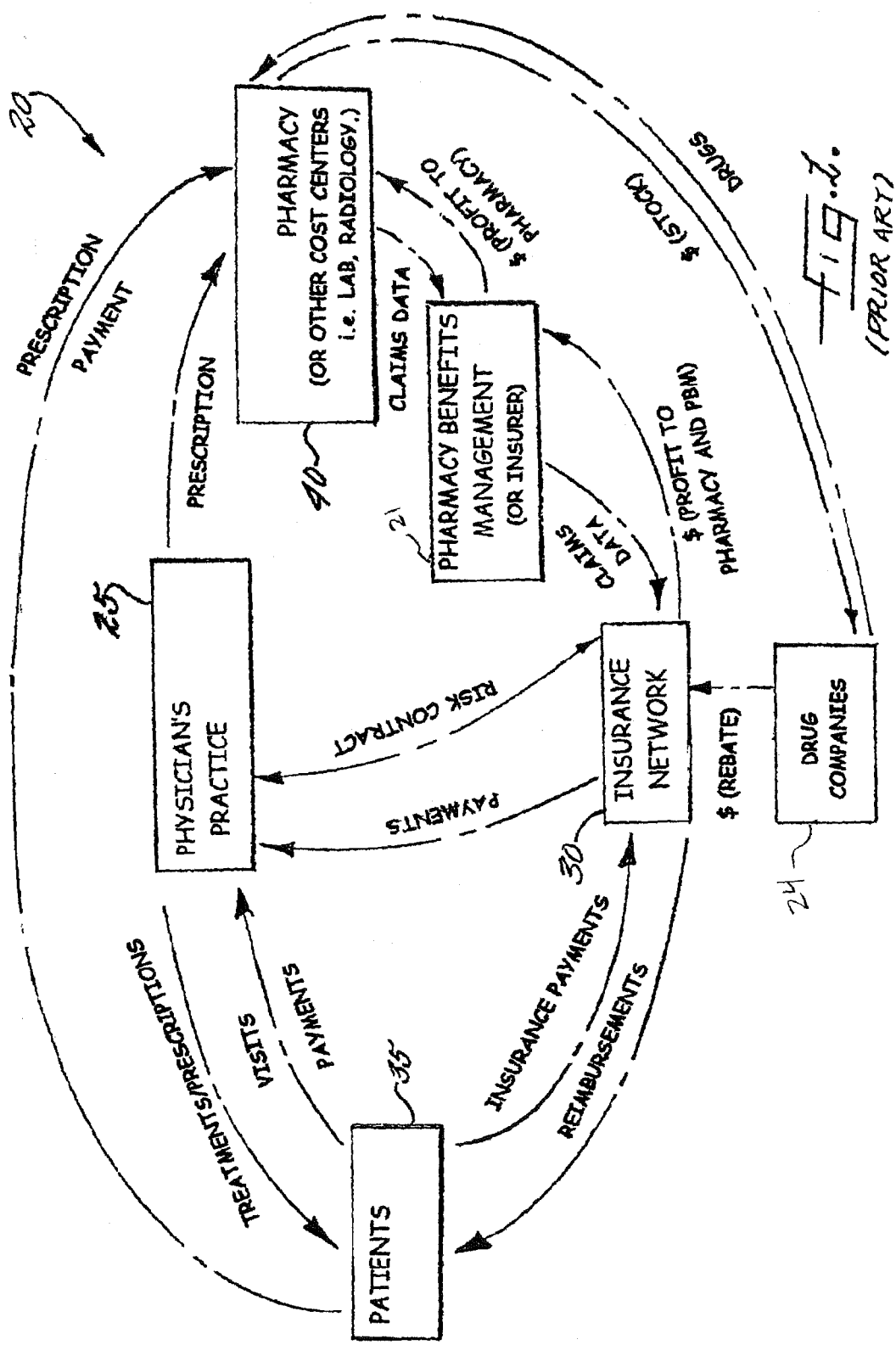
FIG. 1 is a schematic view of a typical relationship between physicians, insurance networks, and patients according to the prior art.

FIGS. 1A-6A illustrate systems and methods of optimizing profitability of healthcare practices and insurance networks by managing ancillary medical costs. As illustrated in FIG. 1A, embodiments of the present invention can include a healthcare consultation group 22 that forms an intermediary relationship between a healthcare practice 25 and an insurance network 30. The healthcare practice 25 preferably includes a plurality of physicians 27 practicing in one or more medical fields in a particular geographic area. The healthcare consultation group 22 determines the most efficient manner to manage ancillary medical costs to thereby increase profitability of the healthcare practice 25 and the insurance network 30 by decreasing ancillary medical costs. In cases where the financial responsibility for patient care is divided between the insurance network 30 and the healthcare practice 25, the healthcare consultation group 22 can also advantageously manage ancillary medical costs of the insurance network 30 and the healthcare practice 25 to thereby decrease ancillary medical costs, thereby increasing profitability of both the insurance network 30 and the healthcare practice 25. Ancillary medical costs can include pharmacy costs, for example. The ancillary medical costs can also advantageously include any one of a number of medical cost centers such as taken from federally-defined hospital departments. These can include, but are not limited to, anesthesiology, blood, blood storage procedure and administration, radiology, electroencephalogram (EEG), electrocardiogram (EKG), emergency room, IV therapy, organ and tissue acquisition, labor and delivery, medical/surgical supplies, nuclear medicine, occupational therapy, operating room, physical therapy, recovery room, renal dialysis, respiratory therapy, special care, speech therapy, and therapeutic radiology. These general categories also can be broken down into more specific categories as understood by those skilled in the art.

As perhaps best illustrated in FIGS. 1A-4, embodiments of the present invention provide methods for managing a healthcare practice 25 to optimize the profitability of the healthcare practice 25 by decreasing the healthcare costs of the healthcare practice 25. As illustrated in FIG. 3, embodiments of the present invention also provide methods of optimizing the profitability of an insurance network 30 having a plurality of physicians 27 in a healthcare practice 25 participating therein by managing ancillary medical costs, i.e., pharmacy costs, of the healthcare practice 25, or a combination of the healthcare practice 25 and the insurance network 30. Various embodiments of the present invention are particularly advantageous for use in association with pharmacy cost because of the large year to year increases in the cost of prescription medications and other pharmaceutical related costs. The method of managing the healthcare practice 25 and the method of optimizing the profitability of the insurance network 30 can include gathering data 50 from each of the plurality of physicians 27 in the healthcare practice 25 participating in the insurance network 30 regarding management of ancillary medical costs. The step of gathering data 50 preferably includes conferring with the healthcare practice 25 and the insurance network 30 to determine 53 the number of patients 35 participating in the insurance network 30 and the current ancillary medical procedure used to treat those patients 35. In a case where the ancillary medical cost is pharmacy cost, for example, the method includes gathering data from the physicians 27 regarding the number of pharmacy claims over a predetermined period of time, the number of patients 35 treated by the physician 27, and demographic information about the physician 27.

Data is also gathered 52 from ancillary medical facilities 40 regarding ancillary medical costs of each of the plurality of physicians 27 in the healthcare practice 25 participating in the insurance network 30. This data can advantageously include claims information, claim types, and cost data regarding the claims. This data can also advantageously be gathered from the healthcare practice 25 or the insurance network 30. The data collected from the ancillary medical facilities 40 can be available on an ancillary medical network database, such as a pharmacy network listing pharmacy costs for each of a plurality of physicians 27 in the healthcare practice 25. Again, in a case where the ancillary medical cost is pharmacy cost, for example, the method of gathering data 50 includes obtaining average wholesale pharmacy costs from pharmacy networks such as First Databank, Red Book, and Blue Book, for example, or any other pharmacy network as understood by those skilled in the art. The step of gathering data 50 from the pharmacy can also include getting monthly updates from the pharmacy network regarding average wholesale pharmacy costs. The step of gathering data 50 further can include extrapolating a contracted price of prescription medications from the pharmacy claims data.

If the ancillary medical cost is a pharmacy cost, for example, then the step of gathering data 50 can advantageously include preparing a management report that includes information regarding the physician's pharmacy cost performance measured by per member per month (PMPM) costs. The management report can also advantageously include a physician report card to inform the physician 27 of current performance and high cost patient reports from the physician 27. The report card is advantageously detailed for each physician 27 based on prescribing patterns, costs of management behavior to them and the healthcare practice 25, peer-reviewed alternative prescription medications, and potential savings if followed. The report cards are then presented to the identified physician 27 so that they can perform their own analysis. The healthcare practice 25 can advantageously encourage the physician 27 to give the report consideration. The management report can also advantageously include a list of the top medication providers, e.g., the top fifty high-cost prescription medication providers and a pharmacy cost management report.

The method of managing the healthcare practice 25 and the method of optimizing the profitability of an insurance network 30 both further can include identifying 56 at least one physician 27 in the healthcare practice 25 that is engaging in ancillary medical procedures that are not as profitable or preferred by the insurance network 30. Physicians 27 who engage in the ancillary medical procedures that are not preferred by the insurance network 30 are sometimes at risk of not receiving a predetermined reimbursement amount from the insurance network 30. These ancillary medical procedures can include the prescription of medications that are not as profitable to the insurance network 30 or the physicians 27 in the healthcare practice 25. In cases where the financial responsibility for patient 35 care is shared between the healthcare practice 25 and the insurance network 30, then the profitability of both the insurance network 30 and the healthcare practice 25 are enhanced. Typically, alternative medications are available that combat the same illnesses. In some instances, however, either the physician is not familiar with the alternative medication or the patient 35 insists on a particular brand-name medication merely because the brand-name medication has been greatly advertised, marketed, or commercialized.

The step of identifying the at least one physician 56 can include analyzing the data 58 collected from the physicians and the ancillary medical network databases to determine the ancillary medical costs of each physician 27 in the healthcare practice 25. The step of identifying the at least one physician 56 also can include calculating 60 an average ancillary medical cost per physician in the healthcare practice 25. After an average is calculated 60, physicians 27 having ancillary medical costs that fall a predetermined standard deviation away from the average, e.g., two standard deviations from the average of their peers in the healthcare practice 25, are identified 56 and targeted for intervention. Should a point be reached where no physician 27 falls beyond the two standard deviation limit, then a predetermined percentage of the physicians having the highest or higher than average ancillary medical costs can be considered for intervention.

The method of managing the healthcare practice group 20 and optimizing the profitability of an insurance network 30 both can further include identifying patients 35 and ancillary medical procedures that have costs above the average ancillary medical cost calculated above. For example, the step of identifying patients 35 whose ancillary medical costs are greater than the average ancillary medical costs per physician 27 can include identifying patients 35 who have pharmacy costs greater than the average pharmacy cost of the physician 27. Another example preferably includes identifying prescription medications having a higher cost than the average prescription medication cost of the healthcare practice 25.

When the physician 27 that has ancillary medical costs greater than the average ancillary medical costs of the healthcare practice 25 is identified, the method of managing the healthcare practice group 20 and the method of optimizing the profitability of an insurance network 30 both can further include conferencing with the identified physician 27 to discuss the impact of not taking any action regarding ancillary medical cost overruns.

The method of managing the healthcare practice 20 and the method of optimizing the profitability of an insurance network 30 both can further include modifying the physician's management behavior 65 regarding the ancillary medical costs. The physician's management behavior can be modified to advantageously reduce the risk of not collecting the predetermined reimbursement amount from the insurance network 30 to thereby increase the physician's profitability. The physician's modified management behavior can also advantageously increase the profitability of the insurance network 30.

The step of modifying the physician's management behavior includes educating 70 the at least one physician 27 on benefits of alternative ancillary medical procedures. The education 70 of the physician 27 can be performed using research literature for comparing the alternative ancillary medical procedures to current ancillary medical procedures. The education 70 can further include organizing continued medical education classes 71 through ancillary medical facilities and can also include the education 72 of nurses and ancillary staff members. This is advantageous because continued medical education classes are generally required in order for a physician 27 to keep licensing requirements current. The continued medical education can advantageously fulfill the physician's licensing requirement while simultaneously educating the physician 27 as to the benefits of alternative ancillary medical procedures that may be more advantageous to themselves as well as to their patients.

The step of educating 70 the at least one physician 27 advantageously includes providing the at least one physician national treatment guidelines for stepwise treatment of disease states. Too often prescription medication representatives, such as sales representatives, convince physicians 27 that the newest medication is necessary to treat patients 35 and other regimens should be skipped or abandoned. The step of educating 70 the physicians 27, therefore, includes recommending that physicians 27 follow nationally recognized guidelines and treatment protocols, such as from the Center for Disease Control (CDC) and the National Institute of Health (NIH), for example.

This advantageously ensures that community accepted standards of care are being provided. The step of educating 70 the physicians 27 also advantageously includes identifying the medications of choice for given disease states and verifying, through data analysis and dialog, that medical research indicates that modified physicians behavior will have a favorable impact. The step of educating 70 the physicians 27 using peer-reviewed, medical research based literature recommending nationally recognized guidelines also advantageously decreases liability incurred by physicians 27. The physicians' 27 medical malpractice liability can advantageously be decreased if the physician follows nationally recognized guidelines and treatment protocols.

The step of modifying the physician's management behavior also includes providing patient history updates. If, for example, the physician 27 makes a decision to modify a patient's 35 prescription medication in the interest of decreasing pharmacy cost, for example, the patient history updates become very advantageous for the general safety and welfare of the patient 27. At the time of ordering the new prescription, physicians 27 may not have all the patient's 35 medical history to prescribe a medication without inducing an adverse drug reaction (ADR). ADR's often lead to increased repeat visits to the physician 27 for the same ailment and possibly to a hospital, which increase the healthcare practice's 25 health care cost tremendously. After the gathered data, provided by a pharmacy benefits management (PBM) company or a pharmacy claims benefit administrator, for example, is analyzed, printouts of the patients' 35 prescription history can advantageously be provided to the physician 27. These printouts may be included in patient 35 charts for up-to-date reference by the physicians 27.

Figure 2A:
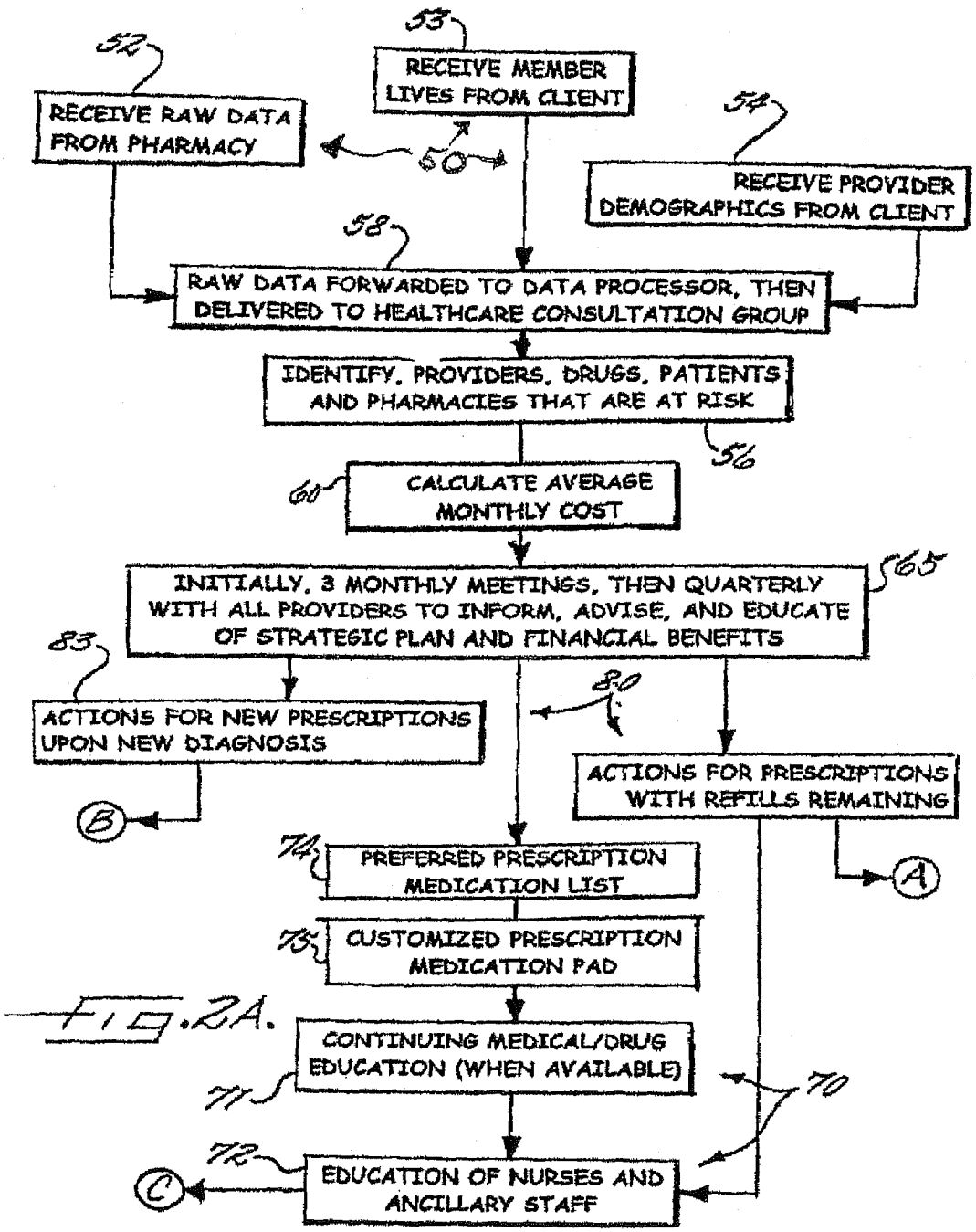
FIG. 2A is a flow chart describing the method of managing ancillary medical costs for healthcare practices and insurance networks according to an embodiment of the present invention.

As best illustrated in FIG. 2A, the method of managing the healthcare practice 25 and the method of optimizing profitability of the insurance network 30 further can include providing a list of ancillary medical procedures, e.g., a list of preferred prescription medications, that are preferred by the insurance network 30. If the physicians 27 follow the suggested ancillary medical procedure list, the physicians 27 are more likely to receive the predetermined reimbursement from the insurance network 30, thereby providing enhanced profits to the physicians 27 as well as to the insurance networks 30. The enhanced profitability advantageously allows the insurance network 30 and the physicians 27 to provide more cost-effective medical treatment to the patients.

As also illustrated in FIG. 2A, the methods of managing the healthcare practice 25 and optimizing profitability of the insurance network 30 also advantageously can include providing custom ancillary medication procedure forms 75, i.e., custom prescription medication pads, for use by the physician 27 to thereby allow the physician to easily recognize which ancillary medical procedures are preferred by the insurance network 30. For example, the physician 27 can be provided a custom prescription medication pad 75 that includes a vast list of prescription medications that are preferred by the insurance network 30. This eliminates the time necessary for the physician 27 to perform research on which medications are preferred by the insurance network 30.

Physicians 27 sometimes participate in a number of insurance networks 30. Differing insurance networks 30 normally have differing preferred ancillary medical procedures. When the physicians 27 participate in differing insurance networks 30, it becomes difficult to determine which ancillary medical procedures are preferred by each of the different insurance networks 30. The various insurance networks 30 normally have overlapping ancillary medical procedures. Therefore, the step of providing custom ancillary medical procedure customization forms also includes the step of providing custom ancillary medical procedure forms that account for the overlapping ancillary medical procedures of the various networks and advantageously eliminate the need for the physician 27 to take the time to research what insurance network 30 the patient 35 participates in and which ancillary medical procedures are preferred by the particular insurance network 30 in which the patient 35 participates. The custom ancillary medical form that accounts for overlapping ancillary medical procedures between various insurance networks 30 advantageously allows the physician 27 to engage in any ancillary medical procedure that is listed on the form without any risk of not receiving the predetermined reimbursement amount from the insurance network 30.

Figure 2B:
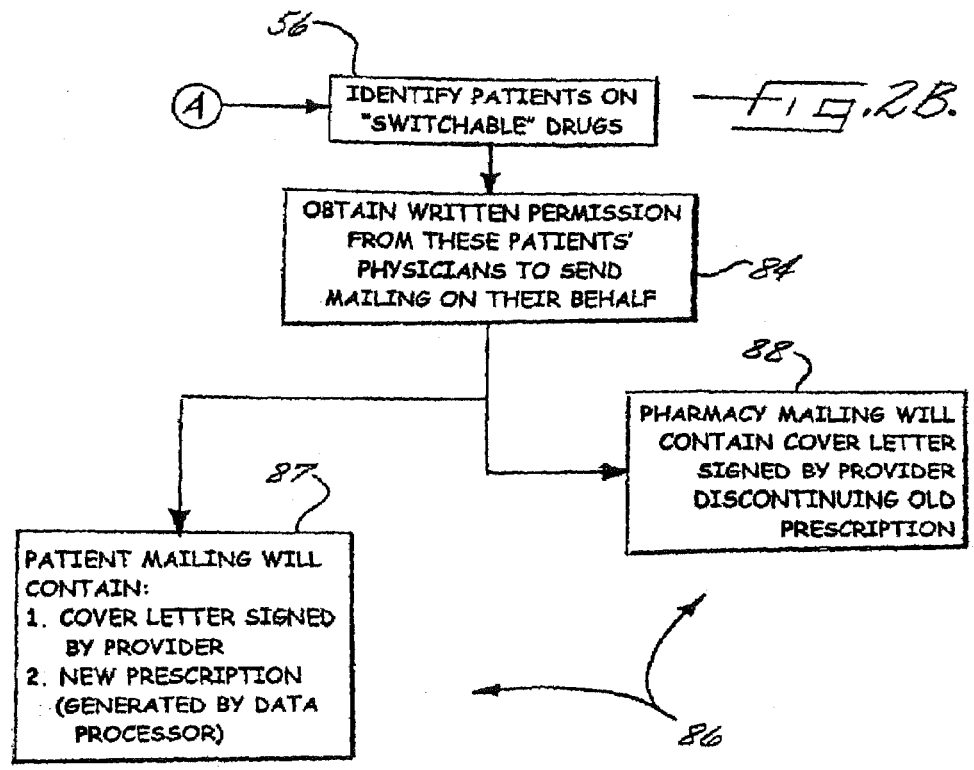
FIG. 2B is a flow chart describing the method of modifying ancillary medical procedures according to an embodiment of the present invention.
Figure 2C:
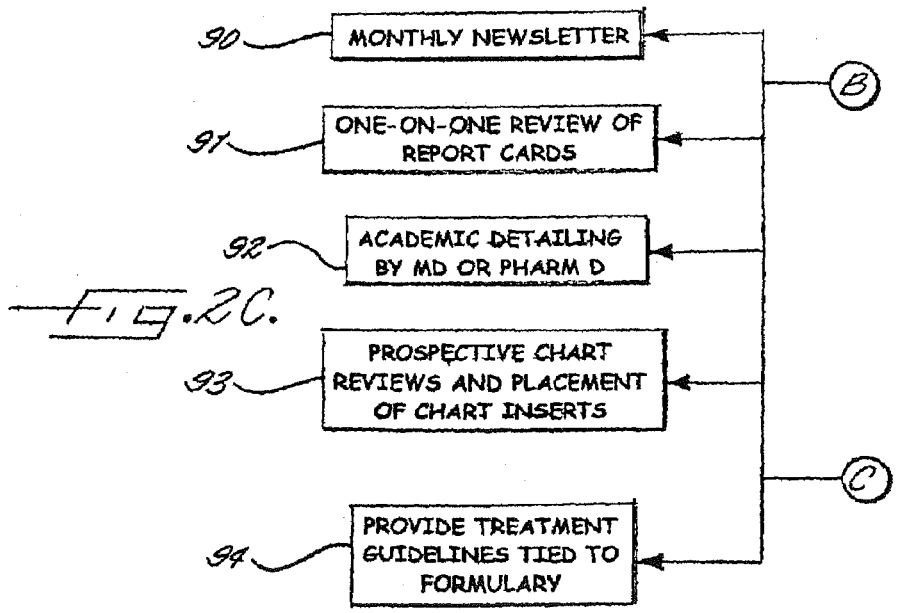
FIG. 2C is a flow chart describing the method of educating physicians on the benefits of alternative ancillary medical procedures according to an embodiment of the present invention.

As best illustrated in FIG. 2A-2C, the methods of managing a healthcare practice 25 and optimizing profitability of an insurance network 30 according to embodiments of the present invention can also include providing patient intervention 80 to enhance the profitability of the physicians 27 and the insurance networks 30. One source of increased ancillary medical costs are unnecessary patient requests. The patients 35 sometimes request particular ancillary medical procedures because of a lack of knowledge regarding alternative ancillary medical procedures. For example, some patients 35 insist on brand-name medications that are largely commercialized without having the requisite knowledge to make an informed decision regarding alternative ancillary medications. The step of providing patient intervention 80 advantageously includes identifying 56 the patients who participate in ancillary medical procedures that are not preferred by the insurance network 30 and put the physician 27 at risk of not receiving a predetermined reimbursement from the insurance network 30. The method of providing the patient intervention 80 also advantageously includes discontinuing the current ancillary medical procedure and amending the current ancillary medical procedure with a new ancillary medical procedure that is preferred by the insurance network 30 and reduces the risk of the physician 27 not receiving the predetermined reimbursement amount from the insurance network 30.

The step of providing patient intervention can advantageously include contacting patients 35 that are affected by poly-pharmacy and non-compliance, for example. The step of contacting patients includes contacting the patients 35 on a monthly basis. Poly-pharmacy occurs when the patient 35 is taking medications with ADRs, unnecessary medications, or those from the same medication class. In addition, if it is discovered during the step of analyzing the gathered data that the patient 35 is not taking the prescription medication as required, the step further includes contacting the patient 35 with a directive to comply with the treatment protocols. The contact to the patient 35 can, for example, be made in the form of a letter written on the physician's 27 letterhead.

The step of providing patient intervention also advantageously can include determining if stronger disease state management techniques are required. This determination is conducted on a monthly basis. For those patients 35 with aggressive diseases, specialist organizations can be employed to provide recommendations to the physicians 27 and the patients 35 on the latest treatments techniques.

The steps of discontinuing and amending current ancillary medical procedures can include providing information to the patients 35 regarding the benefits of the new alternative medical procedure, e.g., information that a lay-patient can understand regarding the benefits of an alternative prescription medication. The step of providing patient intervention can also include providing a monthly review of patient's charts to determine if the new ancillary medical procedures are sufficient for the patient's treatment. As patients are identified 56 that are not being treated per guidelines of alternative ancillary medical procedures, a chart 48 is advantageously inserted into a patient's medical chart, recommending an alternative ancillary medical procedure. The chart insert 48 advantageously includes an explanation of the recommended and pre-written ancillary medical procedure orders, i.e., pre-written prescriptions, for the physician's approval.

The physicians 27, however, do not always yield to the preferred ancillary medical procedures of the insurance network 30. When the physicians 27 encounter a situation where, relying on their vast medical knowledge, they know a proposed ancillary medical procedure is detrimental to the patient 35, then the insurance network 30 is approached to consider modifying their preferred ancillary medical procedures. Like the physicians 27, the insurance network 30 can be educated regarding the benefits of the ancillary medical procedure that they seek to modify. This advantageously levels the playing field between physicians 27 and insurance networks 30. Various embodiments of the present invention provide for the possibility that the insurance network 30 will yield to the medical judgment of the physician 27 concerning the treatment of patients 35.

The step of discontinuing an ancillary medical procedure further can include the step of preparing a plurality of letters 86. The step of preparing the plurality of letters can include the healthcare consultation group 22 obtaining permission 84 from the physician 27 to distribute letters 87 to the patients 35 that are candidates for modification of ancillary medical procedures. One of the plurality of letters informs the ancillary medical facility of the discontinuation of a particular ancillary medical procedure 88. Another of the plurality of letters informs the patient that a particular ancillary medical procedure is discontinued 87. The letters can advantageously be written on the physician's letterhead. The letter to be sent to the patient 35 advantageously can include a detailed explanation of why the ancillary medical procedure is being modified, the benefits of the new ancillary medical procedure, and the advantages that patient 35 will obtain from using the new ancillary medical procedures. The letter to be sent to the ancillary medical facility 88 instructs the ancillary medical facility that the ancillary medical procedure is discontinued and can also advantageously inform the ancillary medical facility of an amendment to the ancillary medical procedure. The step of discontinuing the ancillary medication can also include providing the physician 27 with a list of "frequently asked questions and answers" so that the physician 27 is prepared for what may be difficult questions posed by the patients 35. This advantageously allows the physician 27 to give the patients 35 clear and concise answers that do not make the patient 35 feel as though the physician 27 and the insurance network 30 are taking advantage of the patient.

The step of providing patient intervention also advantageously can include ordering a new alternative ancillary medical procedure upon a new diagnosis 83. The step of ordering a new ancillary medical procedure advantageously includes providing a monthly update 90 to the physicians 27 regarding new alternative ancillary medical procedures. The monthly updates can come in the form of a newsletter, for example. The step of ordering a new ancillary medical procedure also advantageously includes providing a review 91 between the physician 27 and the healthcare consultation group 25 regarding new ancillary medical procedures and education 92 provided to the physicians 27 and patients 35 regarding the new ancillary medical procedures. The patient's chart can be periodically reviewed 93 to ensure that the new ancillary medical procedure is effective, and treatment guidelines can be provided 94 on a chart insert 48, as illustrated in FIG. 6A.

The methods of managing the healthcare practice 25 and optimizing the profitability of the insurance network 30 also advantageously can include updating physicians 27 regarding changes of ancillary medical procedures preferred by the insurance network 30. The step of updating can advantageously include mailing the updated changes to each of the physicians 27 in the healthcare provider group 22 using a newsletter 90, or the step of updating can advantageously include transmitting the changes to the physicians 27 via electronic mail or flyers, or other types of updates. The step of updating can also advantageously include connecting to a communications network 100 to access the updated information. This advantageously eliminates the time necessary for the physicians 27 to research new preferred ancillary medical procedures. The updates are also a form of continuing education for the physician 27 to learn of new techniques and medications that are available to enhance the treatment of the patients 35.

Some healthcare practices 25 have opted to use personal digital assistants (PDAs) or other electronic data entry and retrieval hardware in their practices. For those groups, whenever possible, the hardware and/or software will be integrated with the information and services provided as described above. Allscripts, Parkstone, and Realtime Rx are just a few examples of companies that sell or lease such equipment. This will be done in an effort to disencumber the physicians 27 so they can focus on better management of their time.

As best illustrated in FIGS. 1A, 4, and 5, embodiments of the present invention advantageously can include a healthcare management optimization system 20 for a healthcare practice 25 including a plurality of physicians 27 participating in an insurance network 30. The system can advantageously can include a server 102 with a database 103 and a communications network 100. The system 20 also preferably can include a plurality of computers 108 positioned to be in communication with the communications network 100, each including a user interface responsive to a user. The database 103 can advantageously include first and second databases. The first database can include information regarding preferred ancillary medical procedures of an insurance network. The second database can include ancillary medical costs of a plurality of physicians 27 participating in the insurance network 30. The system can further include an updater positioned on the server 102 and responsive to the user interface for updating each of the plurality of physicians 27 on any changes of preferred ancillary medical procedures preferred by the insurance network 30.

The system 20 according to an embodiment of the present invention can also include an analyzer such as provided by software programs stored on a computer or processor as understood by those skilled in the art, positioned on the server 102 and in communication with the first and second databases for comparing the ancillary medical procedures that are preferred by the insurance network 30 with the ancillary medical costs of the plurality of physicians 27 participating in the insurance network 30. The analyzer can advantageously identify ancillary medical costs of the physicians 27 that are not preferred by the insurance network 30. The analyzer can further include calculating means for calculating an average ancillary medical cost per physician 27 for the healthcare practice 25. The average ancillary medical cost can be used to identify the physicians 27 that are in need of assistance to reduce the risk of not receiving the predetermined reimbursement amount for ancillary medical costs from the insurance network 30.

The system 20 can further include recommending means, e.g., provided by software, as understood by those skilled in the art, positioned on the server 102 and responsive to the user interface for recommending to each of the plurality of physicians 27 alternative ancillary medical procedures that are preferred by the insurance network 30. The recommending means can advantageously be provided by software that resides on the server 102. The system also preferably includes managing means, e.g., provided by software as understood by those skilled in the art, for managing ancillary medical cost management behavior of the physicians 27. The managing means can advantageously be provided by software that resides on the server 102. The managing means can include a modifier to modify the management behavior of the physicians 27 so that the physicians 27 engage in ancillary medical procedures that are preferred by the insurance network 30. The managing means also can include an identifier for identifying at least one of the plurality of physicians 27 in the healthcare practice 25 participating in the insurance network 30 that is at a greater risk of not receiving a predetermined reimbursement amount for the ancillary medical costs from the insurance network 30 because of engagement in ancillary medical procedures that are not as profitable to the insurance network 30.

The system 20 according to an embodiment of the present invention can further include patient intervening means, e.g., provided by software, as understood by those skilled in the art, for identifying at least one patient 35 whose present ancillary medical procedures are not preferred by the insurance network 30. The patient intervening means can advantageously be provided by software that resides on the server 102. The management means of the system 20 can further include generating means, e.g., also preferably provided by software, as understood by those skilled in the art, for generating a plurality of letters to modify the ancillary medical procedures of the physician 27. The letters can include first and second letters. The first letter can inform the ancillary medical facility that the patient's 35 present ancillary medical procedure is modified. The second letter can be sent to the patient 35 to inform the patient of the new ancillary medical procedure. Furthermore, the second letter can include educational information informing the patient 35 of the benefits of the new ancillary medical procedure and educational materials that may answer any questions that the patient 27 may have.

As illustrated in FIG. 3, embodiments of the present invention also provide methods of collecting fees 120 for managing and optimizing the profitability of a plurality of physicians 27 in a healthcare practice 25 and for managing and optimizing the profitability of an insurance network 30. Such a method, for example, includes establishing a relationship 122 between a healthcare consultation group 22, a plurality of physicians 27 in a healthcare practice 25, and an insurance network 30. This advantageously provides a team working towards a common goal, i.e., a team working towards the goal of enhancing profitability through better and more cost-effective healthcare. The newly established relationship can be used to modify the physicians' ancillary medical cost management behavior to enhance the profitability of the insurance network 30 and to reduce the physician's 27 risk of not receiving a predetermined reimbursement amount for ancillary medical costs from the insurance network 30.

The method of collecting fees 120 can advantageously include the step of the healthcare consultation group 22 funding an incentive pool 124 to be paid to the healthcare practice 25, or to the insurance network 30, depending upon who hires the healthcare consultation group 22. The healthcare consultation group 22 only collects a fee if their services to the healthcare practice 25 and the insurance network 30 are successful. Therefore, the fees are only collected on a success-fee basis. In some cases, however, a nominal fee may be charged by the healthcare consultation group 22 before services are performed. The measure of success of the services of the healthcare consultation group 22 is a decrease in healthcare costs of the insurance network 30 and the physicians 27 in the healthcare practice 25 for specific ancillary medical costs. If services of the healthcare consultation group 22, however, do not decrease healthcare costs for the plurality of physicians 27 or the insurance network 30 below a predetermined level over a preselected period of time, the funds in the incentive pool are turned over to the healthcare practice 25 or the insurance network 30, depending on who is the healthcare consultations group's 22 client. This advantageously provides accountability to the healthcare consultation group 22. Accountability will ease the minds of the healthcare practice 25 and insurance network 30 giving the healthcare consultation group 22 a chance to prove that profits can be enhanced.

The method of collecting fees 120 further can include distributing predetermined percentages 126 of savings attributed to the services of the healthcare consultation group 22. As illustrated in FIG. 3, the savings are distributed to the healthcare practice Y, the healthcare consultation group Z, and the insurance network X. For example, the percentages can be 40% to the consultation group. Clearly, these percentages can vary depending on the client of the consultation group and an agreement between the parties. This arrangement advantageously allows all involved to gain, including patients, through more cost-effective medical care. The predetermined percentage that is distributed to the healthcare practice Y can advantageously be further distributed 128 in predetermined percentages evenly to the healthcare practice 25 or allocated proportionately according to the savings 129 of each of the plurality of physicians 27 in the healthcare practice 25.

The step of distributing predetermined percentages 126 of savings attributed to the services of the healthcare consultation group 22 can advantageously vary depending on whether the client of the healthcare consultation group 22 is the healthcare practice 25 or the insurance network 30. The distributed percentages can advantageously be equal between the healthcare consultation group 22, the insurance network 30, and the healthcare practice 25. If, for example, the client of the healthcare consultation group 22 is the healthcare practice 25, then the predetermined percentages distributed to the healthcare consultation group 22 and the healthcare practice 25 can be greater than the predetermined percentage of the savings that are distributed to the insurance network 30, e.g., the insurance network 30 may not collect any percentage of the savings. If, however, the client of the healthcare consultation group 22 is the insurance network 30, then the predetermined percentages distributed to the healthcare consultation group 22 and the insurance network 30 can be greater than the predetermined percentage of the savings that are distributed to the healthcare practice 25.

The method of collecting fees can also advantageously include a pricing, billing, or charging structure. The pricing structure of the healthcare consultation group 22 is straight forward. The clients, i.e., the healthcare practice 25 or the insurance network 30, measure their ancillary medical costs, or pharmacy costs for example, on a per-member per-month (PMPM) basis. During a pharmacy assessment, an average PMPM pharmacy cost (baseline PMPM) is calculated using the clients past six months pharmacy claims and membership data. Each month, the current month's average PMPM pharmacy cost is subtracted from baseline PMPM in order to determine the savings realized from the healthcare consultation group's 22 services.

A commission fee can advantageously be calculated on a predetermined percentage of the monthly client savings, e.g., 50% of monthly savings, multiplied by the number of patients each month. For example, a sustained $1.00 PMPM savings for a client with 30,000 covered lives would yield to the healthcare consultation group 22 $15,000 per month, for up the duration of the contract. The contract can span between one and three years, for example, or can have a longer duration. The healthcare consultation group 22 can collect a smaller fee percentage for longer contract durations. If the client desires a longer contract duration, the baseline PMPM can advantageously be increased yearly with respect to annual inflation increases of wholesale prescription medication costs. The risk reversal for the client is that if there are no savings any month, the client pays nothing.

The pricing structure can also advantageously include a referral commission, e.g., $0.25, for each covered life, or a percentage of the client's savings for example, provided to the strategic marketing partners. This referral commission compensates for the commissions paid to sales people and people who refer business to the healthcare consultation group 22. Thus, the healthcare consultation group 22 minimizes the marketing budget while advantageously maximizing marketing results.

In the drawings and specification, there has been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims. Therefore, it is to be understood that the invention is not to be limited to the illustrated embodiments disclosed, and that modifications and other embodiments are intended to be included within the scope of the appended claims.

This application is a continuation of and claims the benefit of and priority to U.S. patent application Ser. No. 13/540,746, titled "Systems, Computer Programs, and Methods for Controlling Cost of a Healthcare Practice," filed on Jul. 7, 2012, which is a continuation of and claims the benefit of and priority to U.S. patent application Ser. No. 13/103,761, titled "Computer Implemented Method and Computer Program Product for Collecting Fees for an Insurance Network," filed on May 9, 2011, which is a continuation of U.S. patent application Ser. No. 11/924,751, titled "Methods for Collecting Fees for Healthcare Management Group" filed on Oct. 26, 2007, now U.S. Pat. No. 7,941,356, which is a continuation of U.S. patent application Ser. No. 09/812,703 titled "Methods for Collecting Fees for Healthcare Management Group" filed on Mar. 19, 2001, now U.S. Pat. No. 7,401,027, reissued as RE43,550; and is also related to U.S. patent application Ser. No. 09/812,704, titled "Methods and Systems for Healthcare Practice Management" also filed on Mar. 19, 2001, now U.S. Pat. No. 7,398,217, reissued as RE42,508, each of which is incorporated herein by reference in its entirety.

That claimed is:

1. A system to manage costs of one or more physicians in an insurance network, the system comprising:

one or more databases having data of one or more physicians participating in an insurance network associated therewith, the data including one or more ancillary medical procedures used by one or more of the physicians to treat one or more patients and one or more preferred ancillary medical procedures;

one or more processors being positioned in communication with the one or more databases and being configured to process the data; and non-transitory memory encoded with one or more computer programs operable by the one or more processors so that during operations thereof, the one or more processors being operable to perform the following steps:

determining, in a first computer process, baseline costs of one or more of the plurality of ancillary medical procedures used by the plurality of physicians to treat the plurality of patients responsive to data stored in the one or more databases, one or more of the baseline costs being determined by measuring average ancillary medical costs of the one or more ancillary medical procedures on a per-member-per-month basis, and calculating an average of the per-member-per-month basis over a preselected period of time to determine a baseline per-member-per-month of the plurality of ancillary medical costs;

identifying, in a second computer process, one or more of the physicians who has used one or more of the ancillary medical procedure that is not preferred;

generating, in a third computer process, information for the one or more physicians representative of one or more recommended alternative ancillary medical procedures that are preferred;

determining, in a fourth computer process, whether the costs of the one or more physicians have reached at least a predetermined level below a baseline over a preselected period of time;

calculating, in a fifth computer process, a preselected percentage of costs savings responsive to determining the costs of the one or more physicians have reached at least the predetermined level below the baseline, the preselected percentage of cost savings being adapted to be distributed to the one or more physicians responsive to the determined costs of the one or more physicians having reached the at least a predetermined level below the baseline;

determining, in a sixth computer process, a portion of the costs savings attributable to behavior modification of one or more of the plurality of physician by practicing the recommended one or more alternative ancillary medical procedures, the behavior modifications including one or more of: one-on-one review of report cards, placement of one or more chart inserts, a newsletter, treatment guidelines tied to formulas, permission documentation from one or more patient's physicians to communicate with the one or more corresponding patient, communication from one or more ancillary medical procedure provider indicating switch to new ancillary medical procedure, and generation by one or more processors of a new ancillary medical procedure with the ancillary medical procedure provider;

determining, in a seventh computer process, an amount of funds for an incentive pool configured to be distributed to the insurance network responsive to the ancillary medical costs of the one or more physicians not decreasing to the at least a predetermined level of the baseline; and receiving, via an electronic communication network, the preselected percentage of costs savings responsive to costs of the one or more physicians having adopted the one or more recommended ancillary medical procedures.

2. A system as defined in claim 1, wherein the one or more of the physicians is identified by identifying ancillary medical costs associated with one or more of the ancillary medical procedures that fall a predetermined standard deviation away from an average ancillary medical costs from the baseline.

3. A system to manage costs of one or more physicians in an insurance network, the system comprising:
   one or more databases having data of a plurality of physicians participating in an insurance network associated therewith, the data including a plurality of ancillary medical procedures used by one or more of the plurality of physicians to treat one or more of a plurality of patients, costs of one or more of the plurality of ancillary medical procedures, and a plurality of preferred ancillary medical procedures;
   one or more processors being positioned in communication with the one or more databases and being configured to process the data; and
   non-transitory memory encoded with one or more computer programs operable by the one or more processors so that during operations thereof, the one or more processors being operable to perform the following steps:
   measuring, in a first computer process, average ancillary medical costs of one or more of the plurality of ancillary medical procedures used by the plurality of physicians to treat the plurality of patients on a per-member-per-month basis;
   calculating, in a second computer process, an average of the per-member-per-month basis over a predetermined period of time to determine a baseline per-member-per-month of the plurality of ancillary medical cost;
   determining, in a third computer process, a baseline-per-member-per-year using the baseline per-member-per-month of the plurality of ancillary medical costs;
   identifying, in a fourth computer process, at least one of the plurality of physicians who has used one or more of the plurality of ancillary medical procedure that is not preferred;
   generating, in a fifth computer process, information for the at least one of the plurality of physicians representative of one or more recommended alternative ancillary medical procedures that are preferred;
   determining, in a sixth computer process, whether the costs of the plurality of physicians have reached at least a predetermined level below the baseline-per-member-per-year over a predetermined time;
   calculating, in a seventh computer process, a predetermined percentage of costs savings for the plurality of physicians responsive to determining the costs of the plurality of physicians have reached at least the predetermined level below the baseline-per-member-per-year; and
   determining, in an eighth computer process, a portion of the costs savings attributable to behavior modification of one or more of the plurality of physician by practicing the recommended one or more alternative ancillary medical procedures, the behavior modifications including one or more of: one-on-one review of resort cards, placement of one or more chart inserts, a newsletter, treatment guidelines tied to formulas, permission documentation from one or more patient's physicians to communicate with the one or more corresponding patient, communication from one or more ancillary medical procedure provider indicating switch to new ancillary medical procedure, and generation by one or more processors of a new ancillary medical procedure with the ancillary medical procedure provider.

4. A system as defined in claim 3, wherein the non-transitory memory further is encoded with one or more computer programs operable by the one or more processors to perform the step of:
   determining, in a ninth computer process, an amount of funds for an incentive pool configured to be distributed to the insurance network responsive to the ancillary medical costs of the plurality of physicians not decreasing to the at least predetermined level of the baseline-per-member-per-year; and
   distributing, via an electronic communication network, funds from the incentive pool to the insurance network, the funds being a second percentage of costs of the plurality of physicians responsive to the costs not reaching the predetermined level of the baseline-per-member-per-year.

5. A system to manage costs of a plurality of physicians in an insurance network, the system comprising
   one or more databases having data of a plurality of physicians in a healthcare practice participating in an insurance network associated therewith, the data including a plurality of ancillary medical procedures used by one or more of the plurality of physicians to treat one or more of a plurality of patients, costs of one or more of the plurality of ancillary medical procedures, and a plurality of preferred ancillary medical procedures;
   one or more processors configured to process the data; and
   non-transitory memory encoded with one or more computer programs operable by the one or more processors so that during operations thereof, the one or more processors being operable to perform the following steps:
   determining, in a first computer process, baseline costs of one or more the plurality of ancillary medical procedures used by the plurality of physicians to treat the plurality of patients using data stored in the one or more databases, the baseline costs being determined by measuring average ancillary medical costs of the plurality of ancillary medical procedures on a per-member-per-month basis, and
   calculating an average of the per-member-per-month basis over a predetermined period of time to determine a baseline per-member-per-month of the plurality of ancillary medical cost;
   identifying, in a second computer process, at least one of the plurality of physicians who has used one or more of the plurality of ancillary medical procedure that is not preferred for cost management behavior modification of one or more of the plurality of ancillary medical procedures;
   generating, in a third computer process, information for the at least one of the plurality of physicians indicating recommended one or more alternative ancillary medical procedures that are preferred to modify cost management behavior of the at least one of the plurality of physicians in the healthcare practice with respect to management of ancillary medical costs;
   determining, in a fourth computer process, whether the costs of the plurality of physicians have reached at least a predetermined level below the baseline over a predetermined period of time; and
   calculating, in a fifth computer process, a predetermined percentage of costs savings responsive to determining the costs of the plurality of physicians have reached at least the predetermined level below the baseline, at least a portion of the costs savings being attributable to behavior modification of one or more of the plurality of physician by practicing the recommended one or more alternative ancillary medical procedures, and wherein the behavior modifications include one or more of: one-on-one review of report cards, placement of one or more chart inserts, a newsletter, treatment guidelines tied to formulas, permission documentation from one or more patient's physicians to communicate with the one or more corresponding patient, communication from one or more ancillary medical procedure provider indicating switch to new ancillary medical procedure, and generation by one or more processors of a new ancillary medical procedure with the ancillary medical procedure provider.

6. A system as defined in claim 5, wherein the predetermined percentage of cost savings is adapted to be distributed to the plurality of physicians responsive to the determined costs of the plurality of physicians having reached the at least the predetermined level below the baseline.

7. A system as defined in claim 6, wherein the identified at least one of the plurality of physicians has ancillary medical costs of one or more of the plurality of ancillary medical procedures that exceed a certain level.

8. A system as defined in claim 5, wherein the non-transitory memory further is encoded with one or more computer programs operable by the one or more processors to perform the step of:

calculating a billing fee structure for the plurality of physicians by multiplying the predetermined percentage of the savings by a number of patients participating in the healthcare practice and the insurance network.

9. A system as defined in claim 5, wherein the non-transitory memory further is encoded with one or more computer programs operable by the one or more processors to perform the step of:

receiving, via an electronic communication network, from the insurance network the predetermined percentage of costs savings responsive to costs of the plurality of physicians having reached the at least predetermined level below the baseline.

10. A system as defined in claim 5, wherein the non-transitory memory further is encoded with one or more computer programs operable by the one or more processors to perform the step of:

determining, in a sixth computer process, an amount of funds for an incentive pool configured to be distributed to the insurance network responsive to the ancillary medical costs of the plurality of physicians not decreasing to the at least predetermined level of the baseline-per-member-per-year.

11. A system as defined in claim 10, wherein the non-transitory memory further is encoded with one or more computer programs operable by the one or more processors to perform the step of:

distributing, via an electronic communication network, funds from the incentive pool to the insurance network, the funds being a second percentage of costs of the plurality of physicians responsive to the costs not reaching the predetermined level of the baseline-per-member-per-year.

12. A system as defined in claim 5, wherein one or more of the plurality of preferred ancillary medical procedures are based on national guidelines.

13. A system as defined in claim 5, wherein the one or more of the plurality of physicians is identified by identifying ancillary medical costs associated with one or more of the plurality of ancillary medical procedures that fall a predetermined standard deviation away from an average ancillary medical costs from the baseline.

* * * * *